United States Patent [19]
Vasudevan et al.

[11] Patent Number: 6,048,873
[45] Date of Patent: Apr. 11, 2000

[54] TETRAHDROQUINOLIN-2-ONE 6 OR 7-YL, TETRAHDROQUINILIN-2-THIONE 6 OR 7-YL PENTADIENOIC ACID AND RELATED DERIVATIVES HAVING RETINOID-LIKE BIOLOGICAL ACTIVITY

[75] Inventors: Jayasree Vasudevan; Vidyasagar Vuligonda, both of Irvine; Richard L. Beard, Newport Beach; Roshantha A. Chandraratna, Mission Viejo, all of Calif.

[73] Assignee: Allergan Sales, Inc., Irvine, Calif.

[21] Appl. No.: 09/164,949

[22] Filed: Oct. 1, 1998

[51] Int. Cl.$^7$ .......................... C07D 215/00; F61K 31/47
[52] U.S. Cl. ............................. 514/311; 546/165
[58] Field of Search ............................. 546/165; 514/311

[56] References Cited

U.S. PATENT DOCUMENTS

| | | | |
|---|---|---|---|
| 5,455,265 | 10/1995 | Chandraratna | 514/448 |
| 5,616,712 | 4/1997 | Teng et al. | 546/158 |
| 5,663,367 | 9/1997 | Vuligonda et al. | 549/4 |
| 5,672,710 | 9/1997 | Beard et al. | 548/188 |
| 5,675,033 | 10/1997 | Vuligonda et al. | 560/100 |
| 5,739,338 | 4/1998 | Beard et al. | 546/153 |
| 5,750,693 | 5/1998 | Chandraratna | 544/253 |
| 5,817,836 | 6/1998 | Vuligonda | 549/23 |

FOREIGN PATENT DOCUMENTS

| | | |
|---|---|---|
| 93/11755 | 6/1993 | WIPO . |
| 93/21146 | 10/1993 | WIPO . |
| 95/04036 | 2/1995 | WIPO . |
| 96/39374 | 12/1996 | WIPO . |
| 97/09297 | 3/1997 | WIPO . |
| 97/12853 | 4/1997 | WIPO . |

OTHER PUBLICATIONS

Omura, K., Swern D., *Tetrahedron*, 1978, 34, 1651–1660.
Journal of Organic Chemistry (1978), 4750–4758, Ashby.
Cheng et al., Biochemical Pharmacology vol. 22 pp. 3099–3108, 1973.
Klein et al., J. Biol. Chem. 271, 22692–22696 (1996).
Chen et al. (1987) Mol. Cell. Biol. 7, 2745–2752.
de Wet (1987) Mol. Cell. Biol. 7, 725–737.
Nagpal et al., EMBO J. 12, 2349–2360 (1993).
Corey, E. J., Schmidt, G., *Tet. Lett.*, 399, (1979).
Verma & Boutwell, Cancer Research, (1977), 37 2196–2201.
Cancer Research: 1662–1670 (1975), O'Brien.
Feigner P. L. and Holm M. (1989) Focus, vol. 11, No. 2, pp. 1–4.
Heyman et al., Cell 68, 397–406, (1992).
Allegretto et al., J. Biol. Chem. 268, 26625–26633, 1993.
Mangelsdorf et al., The Retinoids: Biology, Chemistry and Medicine, pp. 319–349, Raven Press Ltd., New York, 1994.

*Primary Examiner*—D. Margaret Seaman
*Attorney, Agent, or Firm*—Gabor L. Szekeres; Robert J. Baran; Martin A. Voet

[57] ABSTRACT

Compounds of Formula 1

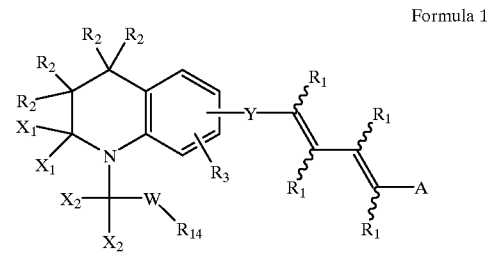

where Y is a bivalent radical having Formula 2 or Formula 3 where o is an integer from 1 to 4

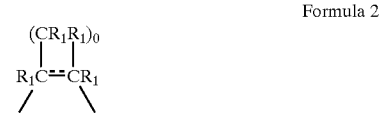

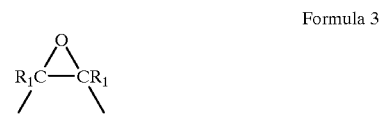

where the remaining symbols have the meaning described in the specification are selective agonists of RXR retinoid receptors.

24 Claims, No Drawings

TETRAHDROQUINOLIN-2-ONE 6 OR 7-YL, TETRAHDROQUINILIN-2-THIONE 6 OR 7-YL PENTADIENOIC ACID AND RELATED DERIVATIVES HAVING RETINOID-LIKE BIOLOGICAL ACTIVITY

BACKGROUND OF THE INVENTION

1. Field of the Invention

The present invention relates to novel compounds having retinoid-like biological activity. More specifically, the present invention relates to compounds that include a substituted tetrahydroquinoline moiety and a 2,4-pentadienoic acid moiety and have selective activity for retinoid X (RXR) receptors.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in is the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists.

Published PCT application WO 97/09297, assigned to the same assignee as the present application, describes several compounds having retinoid antagonist and retinoid inverse agonist type biological activity, and discloses that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well.

Numerous compounds having selective agonist-like activity for RXR retinoid receptors are described in published PCT applications WO 93/21146, WO 95/04036 and WO 97/12853. In these PCT publications specific compounds of particular interest as background to the present invention are, in the WO 93/21146 reference: 4-[1-(3,5,5,8,8-pentamethyl-5,6,7,8-tetrahydro-2-naphthyl)epoxy]benzoic acid, 4-[1-(3,5,5,8,8-pentamethyl-5,6,7,8-tetrahydro-2-naphthyl)cyclopropyl]benzoic acid, 2-[1-(3,5,5,8,8-pentamethyl-5,6,7,8-tetrahydro-2-naphthyl)cyclopropyl] pyridine-5-carboxylic acid and methyl 2-[1-(3,5,5,8,8-pentamethyl-5,6,7,8-tetrahydro-2-naphthyl)cyclopropyl] pyridine-5-carboxylate (Compounds 47, 48, 62 and Me-62 on pages 15 and 17 of WO 93/21146);

in the WO 95/04036 reference: (2E,4E)-3-methyl-5-[1-(3,5,8,8-pentamethyl-5,6,7,8-tetrahydro-2-naphthyl) cyclopropyl]penta-2,4-dienoic acid (Compound 104 on page 23 of WO 95/04036).

In the WO 97/12853 reference: 4-(3,4,6,7,8,9-hexahydro-2-oxo-6,6,9,9-tetramethyl-2H-benzo[g]quinolin-1-ylmethyl)-benzoic acid (Compound 134); 4-(3,4,6,7,8,9-hexahydro-6,6,9,9-tetramethyl-2H-benzo[g]quinolin-1-ylmethyl)-benzoic acid (Compound 135); tetramethyl-3-propyloxy-5,6,7,8-tetrahydronaphthalen-2-yl) cyclopropan-1-yl]-3-methyl hexadienoic acid (Compound 152); (2E, 4E)-6-[2-(5,5,8,8-tetramethyl-3-heptyloxy-5,6,7,8-tetrahydronaphthalen-2-yl) cyclopropan-1-yl]-3-methyl hexadienoic acid (Compound 153); (2E, 4E)-6-[2-(5,5,8,8-tetramethyl-3-benzyloxy-5,6,7,8-tetrahydronaphthalen-2-yl) cyclopropan-1-yl]-3-methyl hexadienoic acid (Compound 154); (2E, 4E)-7-[(5,5,8,8-tetramethyl-3-propyloxy-5,6,7,8-tetrahydronaphthalen-2-yl) cyclopropan-1-yl]-3-methyl heptadienoic acid (Compound 155); (2E, 4E)-7-[(5,5,8,8-tetramethyl-3-heptyloxy-5,6,7,8-tetrahydronaphthalen-2-yl) cyclopropan-1-yl]-3-methyl heptadienoic acid (Compound 156); (2E, 4E)-7-[(5,5,8,8-tetramethyl-3-benzyloxy-5,6,7,8-tetrahydronaphthalen-2-yl) cyclopropan-1-yl]-3-methyl heptadienoic acid (Compound 157); (2E, 4E)-5-[2-(5,5,8,8-tetramethyl-3-propyloxy-5,6,7,8-tetrahydronaphthalen-2-yl) cyclopent-1-en-1-yl]-3-methyl pentadienoic acid (Compound 158); cis (2E, 4E)-5-[2-(5,5,8,8-tetramethyl-3-propyloxy-5,6,7,8-tetrahydro-2-naphthyl) cyclopentan-1-yl]-3-methyl pentadienoic acid (Compound 159).

The following prior art compounds are also of interest to the present invention: (2E, 4E)-6-[1-(5,5,8,8-tetramethyl-5,6,7,8-tetrahydronaphthalen-2-yl) cyclopropan-1-yl]-3-methyl hexadienoic acid (Compound 101); (2E, 4E)-6-[(3,5,5,8,8-pentamethyl-5,6,7,8-tetrahydronaphthalen-2-yl) cyclopropan-1-yl]-3-methyl hexadienoic acid (Compound 102); (2E, 4E)-6-[(5,5,8,8-tetramethyl-3-methoxy-5,6,7,8-tetrahydronaphthalen-2-yl) cyclopropan-1-yl]-3-methyl hexadienoic acid (Compound 103); (2E, 4E)-6-[(5,5,8,8-tetramethyl-3-ethoxy-5,6,7,8-tetrahydronaphthalen-2-yl) cyclopropan-1-yl]-3-methyl hexadienoic acid (Compound 104); (2E, 4E)-6-[(3,5-di-t-butyl phenyl) cyclopropan-1-yl]-3-methyl hexadienoic acid (Compound 105); (2E, 4E)-6-[(3,4-diethyl phenyl) cyclopropan-1-yl]-3-methyl hexadienoic acid (Compound 106); (2E, 4E)-6-[1-(6-t-butyl-1,1-dimethyl-indan-4-yl)-cyclopropyl]-3-methyl hexadienoic acid (Compound 107); and (2E, 4E)-6-[(5,5,8,8-tetramethyl-5,6,7,8-tetrahydronaphthalen-2-yl) cyclopentane-1-yl]-3-methyl hexadienoic acid (Compound 108).

The publication WO 96/39374 published on Dec. 12, 1996 (corresponding to U.S. Pat. Nos. 5,663,367 and 5,675,033) describes 2,4-pentadienoic acid derivatives having selective activity for retinoid RXR receptors. The compounds of this reference include a condensed cyclic (tetrahydronaphthyl, chromanyl, thiochromanyl or N-alkyl-substituted tetrahydroquinoline) moiety, and a cycloayl (primarily cyclopropyl) or phenyl or heteroaryl moiety linking the pentadienoic acid moiety to the condensed cyclic moiety.

U.S. Pat. Nos. 5,750,693 and 5,672,710 disclose certain tetrahydroquinoline derivatives having retinoid-like biological activity.

U.S. Pat. No. 5,739,338 discloses certain N-aryl or N-heteroaryl-substituted tetrahydroquinolines, tetrahydroquinolin-2-ones and 2-thiones having retinoid-agonist, antagonist or inverse agonist-like biological activity.

U.S. Pat. No. 5,616,712 discloses certain N-arylalkyl and N-heteroarylalkyl substituted tetrahydroquinolin-2-ones and 2-thiones having retinoid-like biological activity.

SUMMARY OF THE INVENTION

The present invention relates to compounds of Formula 1,

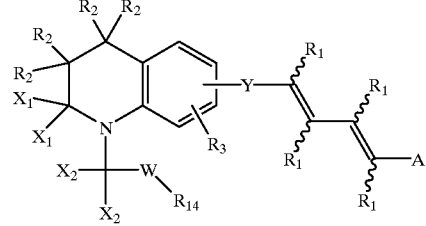

Formula 1 where Y is a bivalent radical having Formula 2 or Formula 3 where o is an integer from 1 to 4

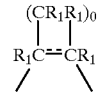

Formula 2

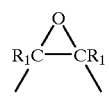

Formula 3 or Y is a bivalent aryl or 5 or 6 membered heteroaryl radical having 1 to 3 heteroatoms selected from N, S and O, said aryl or heteroaryl groups being unsubstituted, or substituted with 1 to 3 $C_{1-6}$ alkyl or with 1 to 3 $C_{1-6}$ fluoroalkyl groups;

the two $X_1$ groups jointly represent an oxo (=O) or thione (=S) function, or $X_1$ is independently selected from H or alkyl of 1 to 6 carbons;

the two $X_2$ groups jointly represent an oxo (=O) or a thione (=S) function, or $X_2$ is independently selected from H or alkyl of 1 to 6 carbons, with the proviso that one of the joint $X_1$ grouping or of the joint $X_2$ grouping represents an oxo (=O) or a thione (=S) function;

W is H, O, $C(R_1)_2$, phenyl, naphthyl, or 5 or 6 membered heteroaryl group having 1 to 3 heteroatoms, said heteroatoms being selected from a group consisting of O, S, and N, said phenyl, naphthyl or heteroaryl groups being unsubstituted or substituted with a $C_1$ to $C_{10}$ alkyl group, with a $C_1$ to $C_{10}$ fluoroalkyl group, or with halogen;

$R_1$ is independently H, lower alkyl of 1 to 6 carbons, or lower fluoroalkyl of 1 to 6 carbons;

$R_2$ is independently H, lower alkyl of 1 to 6 carbons, or lower fluoroalkyl of 1 to 6 carbons;

$R_3$ is hydrogen, lower alkyl of 1 to 6 carbons, $OR_1$, fluoro substituted lower alkyl of 1 to 6 carbons or halogen, $NO_2$, $NH_2$, $NHCO(C_1-C_6$ alkyl, or $NHCO(C_1-C_6)$alkenyl;

A is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CH(OR_{13}O)$, $-COR_7$, $CR_7(OR_{12})_2$, $CR_7(OR_{13}O)$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is H, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_{1-C10}$-alkylphenyl, naphthyl, $C_1-C_{10}$-alkylnaphthyl, phenyl-$C_1-C_{10}$alkyl, naphthyl-$C_1-C_{10}$-alkyl, $C_1-C_{10}$-alkenylphenyl having 1 to 3 double bonds, $C_1-C_{10}$-alkynylphenyl having 1 to 3 triple bonds, phenyl-$C_1-C_{10}$alkenyl having 1 to 3 double bonds, phenyl-$C_1-C_{10}$alkynyl having 1 to 3 triple bonds, hydroxy alkyl of 1 to 10 carbons, hydroxyalkenyl having 2 to 10 carbons and 1 to 3 double bonds, hydroxyalkynyl having 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds where the acyl group is represented by $COR_8$, or $R_{14}$ is a 5 or 6 membered heteroaryl group having 1 to 3 heteroatoms, said heteroatoms being selected from a group consisting of O, S, and N, said carbocyclic aryl and heteroaryl groups being unsubstituted or substituted with a $C_1$ to $C_{10}$ alkyl group, with a $C_1$ to $C_{10}$ fluoroalkyl group, or with halogen, and the dashed line in Formula 2 represents a bond or absence of a bond, with the proviso that when the dashed line represents a bond then there are no $R_1$ substituents on the carbons connected by said bond..

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested. These assays are expected to demonstrate that the compounds of the present invention are primarily selective agonists of RXR receptors in preference over RAR receptors. However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also to expressed in $EC_{50}$ numbers (nanomolar concentration).

RAR-P-GR Holoreceptor Transactivation Assay

CV-1 cells ($4\times10^5$ cells/well) were transiently transfected with the luciferase reporter plasmid MTV-4(R5G)-Luc (0.7 ug/well) containing four copies of the R5G retinoid DNA response element along with the $RXR_\alpha$ expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference.

In this assay, retinoid inverse agonists are able to repress the basal activity of a $RAR_\gamma$-VP-16 chimeric receptor where the constituitively active domain of the herpes simplex virus (HSV) VP-16 is fused to the N-terminus of $RAR_\gamma$. CV-1 cells are cotransfected with $RAR_\gamma$-VP-16, an ER-RXRα chimeric receptor and an ERE-tk-Luc chimeric reporter gene to produce a basal level of luciferase activity, as shown by Nagpal et al. EMBO J. 12, 2349–2360 (1993) expressly incorporated herein by reference. Retinoid inverse agonists are able to inhibit the basal luciferase activity in these cells in a dose dependent manner and $IC_{50}$s measured.

Table 1 discloses data demonstrating the ability of exemplary compounds of the invention to bind to and transactivate through RXR receptors.

TABLE 1

RXR RECEPTOR TRANSACTIVATION AND BINDING DATA:

| Compound # | | RXR α | RXR β | RXR γ |
|---|---|---|---|---|
| 1 | $EC_{50}$ nM | 0.077 | 0.627 | 0.085 |
|   | % Eff | 107 | 109 | 115 |
|   | $K_d$ nM | 1.4 | $ND^1$ | 3.1 |
| 2 | $EC_{50}$ nM | 0.064 | 0.376 | 0.059 |
|   | % Eff | 160 | 144 | 137 |
|   | $K_d$ nM | 0.97 | $ND^1$ | 10.5 |
| 17 | $EC_{50}$ nM | 0.00015 | 0.00042 | 0.00031 |
|   | % Eff | 110 | 115 | 101 |
|   | $K_d$ nM | 0.35 | $ND^1$ | 4.1 |

$^1$ND — not determined

Table 2 discloses data demonstrating that the exemplary compounds of the invention do not bind to, or bind only very weakly to RAR receptors.

TABLE 2

RAR RECEPTOR TRANSACTIVATION AND BINDING DATA:

| Compound # | | RAR α | RAR β | RAR γ |
|---|---|---|---|---|
| 1 | $EC_{50}$ nM | $ND^1$ | $ND^1$ | $ND^1$ |
|   | % Eff | $ND^1$ | $ND^1$ | $ND^1$ |
|   | $K_d$ nM | >10,000 | >10,000 | >10,000 |
| 2 | $EC_{50}$ nM | $ND^1$ | $ND^1$ | $ND^1$ |
|   | % Eff | $ND^1$ | $ND^1$ | $ND^1$ |
|   | $K_d$ nM | 27,000 | 31,000 | 25,000 |
| 17 | $EC_{50}$ nM | $ND^1$ | $ND^1$ | $ND^1$ |
|   | % Eff | $ND^1$ | $ND^1$ | $ND^1$ |
|   | $K_d$ nM | >30,000 | 10,000 | 12,000 |

$^1$ND — not determined

Modes of Administration

The compounds of this invention may be administered systemically or topically, depending on such considerations as the condition to be treated, need for site-specific treatment, quantity of drug to be administered, and numerous other considerations. Inasmuch as the preferred compounds of the invention are primarily RXR selective agonists, the preferred compounds are administered as retinoids.

Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection. Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be administered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where A of Formula 1 is —COOH, this term covers the products derived from treatment of this function with alcohols or thiols preferably with aliphatic alcohols having 1-6 carbons. Where the ester is derived from compounds where A is —CH$_2$OH, this term covers compounds derived from organic acids capable of forming esters including phosphorus based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Many compounds of the present invention have trans and cis (E and Z) isomers. Specific orientation of substituents relative to a double bond is indicated in the name of the respective compound, and/or by specifically showing in the structural formula the orientation of the substituents relative to the double bond.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

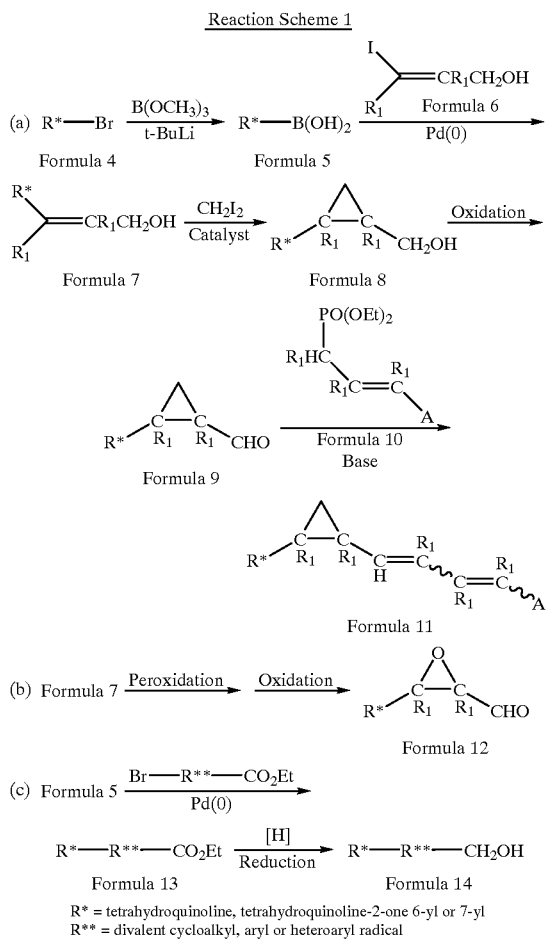

R* = tetrahydroquinoline, tetrahydroquinoline-2-one 6-yl or 7-yl
R** = divalent cycloalkyl, aryl or heteroaryl radical A generalized methodology for obtaining the compounds of the invention is illustrated in Reaction Scheme 1. As is shown in section (a) of this scheme, compounds of the invention where Y is a cyclopropyl function within the definitions of Formula 1 are generally obtained in a sequence of reactions which initially utilizes a halogen (preferably bromine) substituted tetrahydroquinoline derivative (Formula 4) where the halogen atom (preferably bromine as is specifically shown in the scheme) is positioned on the aromatic portion of the tetrahydroquinoline, or tetrahydroquinoline-2-one (as applicable) condensed ring. In the depiction of the compounds of Formula 4 as well as in the entire Reaction Scheme 1, R* represents a substituted tetrahydroquinoline or substituted tetrahydroquinoline-2-one residue where the bromine is in the 6 or 7 position of the tetrahydroquinoline, or tetrahydroquinoline-2-one ring.

The brominated tetrahydroquinoline or tetrahydroquinoline-2-one (as applicable) derivatives of Formula 4 shown in Reaction Scheme 1 as the starting compounds may be available in accordance with prior art patent and/or scientific literature, or may be synthesized in accordance with the synthetic schemes illustrated in connection with the below described specific embodiments, or with such modifications of the below described specific schemes that will become readily apparent to the practicing organic chemist in light of the present disclosure.

Thus, in accordance with the general synthetic methodology, the above-noted halogen, preferably bromine, substituted tetrahydroquinoline or tetrahydroquinoline-2-one derivative of Formula 4 is reacted with trimethoxy boron ($(CH_3O)_3B$) in the presence of tertiary butyl lithium. The resulting tetrahydroquinoline-6-yl, tetrahydroquinoline-7-yl, tetrahydroquinoline-2-one-6-yl or 7-yl boronic acid (as applicable, Formula 5) is therafter reacted in the presence of palladium catalyst (Pd(0)) with a 3-iodo-allyl alcohol derivative (Formula 6) to yield a prop-2-en-1-ol derivative (Formula 7) that is substituted in the 3 position of the propen-1-ol moiety with the tetrahydroquinoline or tetrahydroquinoline-2-one derivative radical.

The cyclopropane ring is introduced into the prop-2-en-1-ol derivative of Formula 7 in a cyclopropylation reaction with diiodomethane in the presence of appropriate catalyst to yield a cyclopropyl derivative of Formula 8. The cyclopropylation reaction is preferably performed in the presence of an enantio selective catalyst. The tetrahydroquinoline-yl-cyclopropyl-methanol derivative of Formula 8 may be resolved by esterification with (1S)-camphanic chloride, isolation of the resulting predominant diastereomer, followed by saponification to provide an optically pure single isomer where the original stereochemistry of the double bond of the allyl alcohol of Formula 6 is retained. The steps of resolving the tetrahydroquinoline-yl-cyclopropyl-methanol derivative of Formula 8 into an optically pure single isomer are not shown in Reaction Scheme 1, but are described in detail in connection with the specific embodiments.

In the next step the primary alcohol function of the tetrahydroquinoline-yl-cyclopropyl-methanol derivative of Formula 8 is oxidized to the aldehyde stage (Formula 9), and the aldehyde compound of Formula 9 is reacted in a Horner Emmons reaction with a diethylphosphono reagent (Formula 10) that has a double bond on a carbon adjacent to the carbon bearing the diethylphosphono group. Consequently, as a result of the Horner Emmons reaction, the conjugated diene moiety of the compounds of the invention (Formula 11) is formed. In as much as the diethylphosphono reagent (Formula 10) also bears the A function (as defined above) of the compounds of the invention, or such precursors of the A function that can be readily converted to the A group by reactions well known in the art, the above-described Horner-Emmons reaction provides compounds of the invention where the Y group of Formula 1 represents cyclopropyl.

Section (b) of Reaction Scheme 1 shows that compounds of the invention where Y represents an oxiranyl (epoxide) ring instead of cyclopropyl, can be made by methods similar to the above described methodology except that instead of cyclopropylating, the compounds of Formula 7 are epoxidized using reagents well known in the art, for example using meta-chloroperoxybenzoic acid. The resulting oxiranyl (epoxide) compound that has a primary alcohol is oxidized to the aldehyde stage (Formula 12) with state-of-the-art reagents, and the aldehyde is subjected to a Horner Emmons reaction, as shown above, to yield the oxiranyl (epoxide) compounds of the invention. The Horner Emmons reaction that is performed on the oxiranyl compounds of Formula 12 is not shown in the reaction scheme.

Compounds of the invention where the Y group is aryl, heteroaryl or cycloalkyl other then cyclopropyl can, generally speaking, be obtained from the boronic acid derivatives as shown in section (c) of Reaction Scheme 1. In this scheme R** represents a bivalent aryl, heteroaryl or cycloalkyl, other than cyclopropyl, radical as these are defined in connection with Formula 1. In accordance with this generalized scheme, the boronic acid derivative of Formula 5 is coupled in the presence of palladium (Pd(0)) catalyst with a halogenated, preferably brominated, cycloalkyl, aryl or heteroaryl carboxylic acid ester. The carboxylic acid ester function of the resulting compound (Formula 13) is reduced to the primary alcohol stage (Formula 14). The primary alcohol of Formula 14 is thereafter treated in the same reaction sequence (oxidation, followed by Horner Emmons reaction) as described above, to provide compounds of the invention.

Details of the above-outlined generalized synthetic schemes are provided below in connection with the description of the specific embodiments.

The synthetic methodology employed for the synthesis of the compounds of the present invention may also include transformations of the group designated A in Formula 1. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K, Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

SPECIFIC EMBODIMENTS

With reference to the symbols $X_1$ and $X_2$ in the Formula 1, preferred compounds of the invention are those where one of the $X_1$ or of the $X_2$ groups represents an oxo (=O) or thione (=S) function, and the remaining one represents lower alkyl or hydrogen, even more preferably hydrogen.

The R, groups of the compounds of the present invention preferably and independently from one another are H or lower alkyl and even more preferably and independently from one another H or methyl. Still more preferably, the two $R_2$ groups in the 4 position of the tetrahydroquinoline, tetrahydroquinoline-2-one or tetrahydroquinoline-2-thione ring are both methyl.

The $R_3$ groups of the preferred compounds of the invention are H or lower alkyl; among lower alkyl methyl is preferred. In the presently most preferred compounds of the invention the $R_3$ group is hydrogen; in other words in the presently most preferred compounds the aromatic portion of the tetrahydroquinoline, tetrahydroquinoline-2-one or tetrahydroquinoline-2-thione condensed ring has only the "Y-dienoic acid" radical as a substituent that is in the 6 or 7 position of the ring.

Referring now to the "W—$R_{14}$" radical in Formula 1, in the preferred compounds of the invention this radical represents H, an alkyl group, an alkyl-aryl or alkyl-heteroaryl group, where aryl is preferably phenyl and heteroaryl is preferably pyridyl, thienyl or furyl. In other preferred compounds of the invention W is —O— and $R_{14}$ is alkyl, aryl or heteroaryl. In these latter type of compounds branch-chained alkyl, especially t-butyl is particularly preferred for $R_{14}$.

The $R_1$ groups of the cycloalkyl and of the oxiranyl rings, as shown in Formulas 2 and 3 are preferably H or lower allyl, even more preferably H, methyl, ethyl or n-propyl. The $R_1$ groups attached to the diene moiety are also preferably H or lower alkyl, even more preferably H or methyl.

The Y group is preferably cyclopropyl, as represented by Formula 2 where o is 1 and the dashed line represents absence of a bond, or Y is oxiranyl as represented by Formula 3. Alternatively the Y group is preferably cyclohexyl, cyclopentyl, phenyl, pyridyl, thienyl, furyl or thiazolyl.

When the Y group is cycloalkyl, as represented by Formula 2, then the diene moiety and the tetrahydroquinoline, tetrahydroquinoline-2-one or tetrahydroquinoline-2-thione radical, as applicable, are preferably in cis orientation relative to the cycloalkyl ring. When the Y group is aryl or heteroaryl then the diene moiety and the tetrahydroquinoline, tetrahydroquinoline-2-one or tetrahydroquinoline-2-thione radical, as applicable, are preferably in ortho or 1,2 orientation relative to the aryl or heteroaryl ring, as applicable.

The A group is preferably COOH, a pharmaceutically acceptable salt of the carboxylic acid, $COOR_8$ or $CONR_9R_{10}$ where $R_8$ are preferably lower alkyl, even more preferably methyl or ethyl.

The double bonds of the diene moiety preferably are in trans orientation.

Attachment of the Y moiety to the tetrahydroquinoline, tetrahydroquinoline-2-one or tetrahydroquinoline-2-thione ring is preferably in the 6 or 7 position of the ring.

In a highly preferred class of compounds of the invention the moiety that is attached to the tetrahydroquinoline, tetrahydroquinoline-2-one or tetrahydroquinoline-2-thione ring, is the group that is depicted below in Formula 15. In this formula $R_1^*$ is methyl, ethyl or n-propyl, presently most preferably methyl. It can be seen that in this moiety the orientation about the cyclopropane ring is cis, and the orientation of both double bonds of the diene moiety is trans. Formula 15 also shows the numbering of the cyclopropane ring and of the pentadienoic acid moiety.

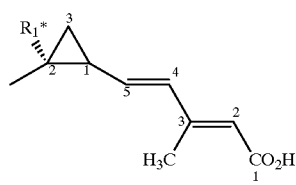

Formula 15

$R_1^*$ = $CH_3$ or $C_2H_5$ or $C_3H_7$

The most preferred class of compounds of the invention are identified below in Table 3 with reference to Formulas 16 and 17.

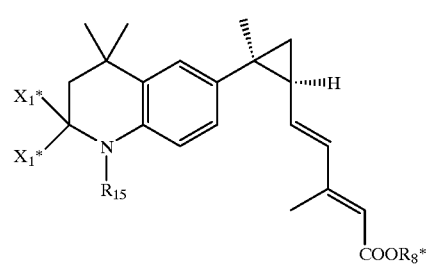

Formula 16

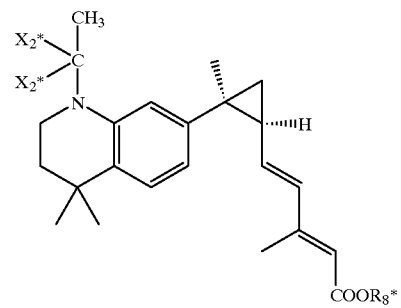

Formula 17

TABLE 3

| Compound # | Formula | $X_1^*, X_1^*$ | $R_{15}$ | $X_2^*, X_2^*$ | $R_8^*$ |
|---|---|---|---|---|---|
| 1 | 16 | =O[1] | iso-propyl | — | H |
| 15 | 16 | =O[1] | iso-propyl | — | ethyl |
| 16 | 16 | =S[2] | iso-propyl | — | ethyl |
| 2 | 16 | =S[2] | iso-propyl | — | H |
| 17 | 16 | H, H[3] | t-butyl-O—CO— | — | H |
| 25 | 16 | H, H[3] | t-butyl-O—CO— | — | ethyl |
| 40 | 16 | H, H[3] | $CH_3$—CO— | — | H |
| 43 | 16 | H, H[3] | $CH_3$—O— | — | ethyl |
| 26 | 17 | — | — | =O[4] | H |
| 36 | 17 | — | — | =O[4] | ethyl |

[1]the two $X_1^*$ groups jointly represent an oxo (=O) group;
[2]the two $X_1^*$ groups jointly represent a thione (=S) group;
[3]both $X_1^*$ groups are H;
[4]the two $X_2^*$ groups jointly represent an oxo (=O) group;

The chemical names of the presently most preferred compounds of the invention, identified in Table 3 are provided in the experimental section of this application.

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all compounds of the invention.

Reaction Scheme 2
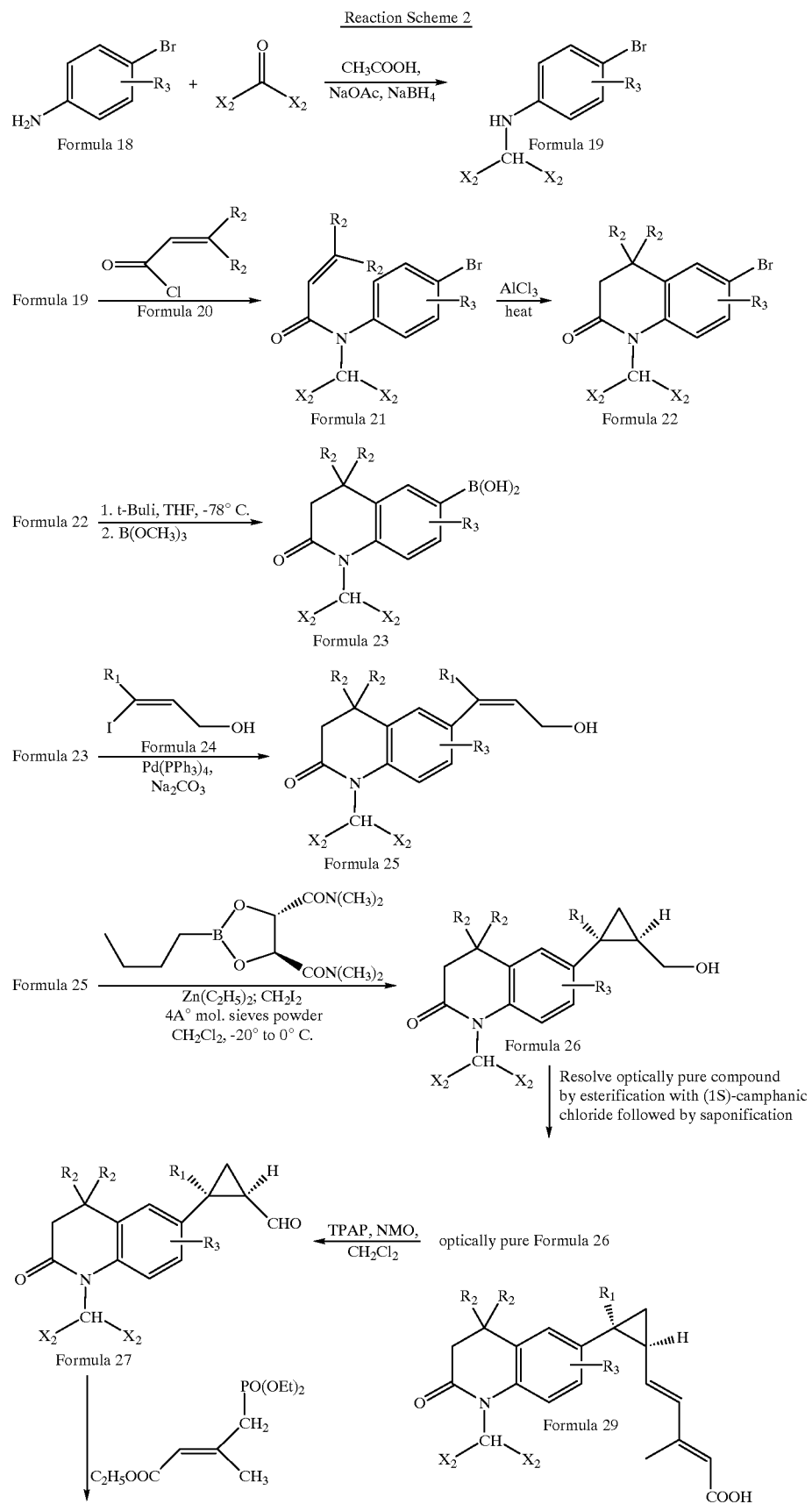

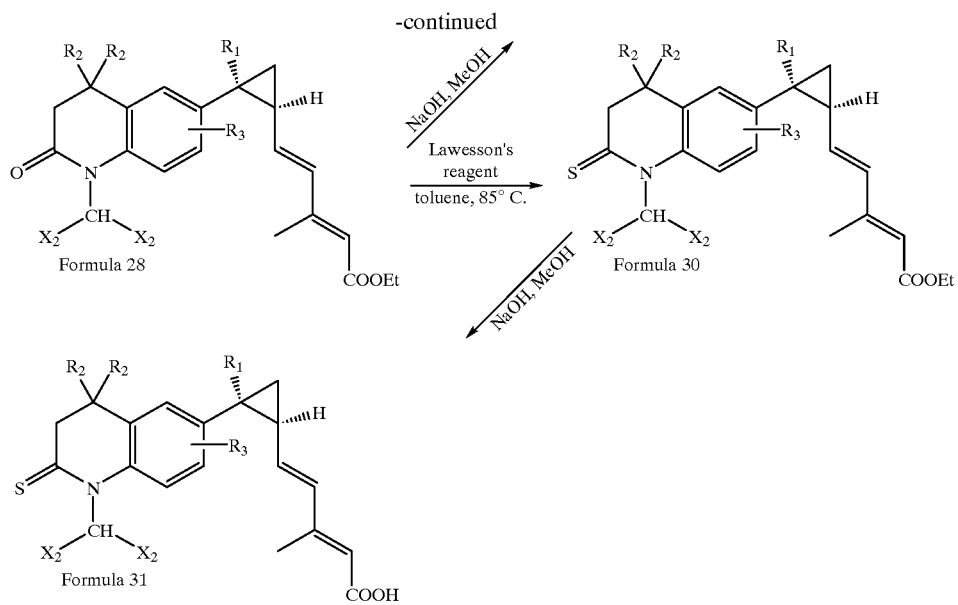

Referring now to Reaction Scheme 2, the synthesis of a preferred class of compounds of the present invention is shown, which fall within the general definition of Formula 1, where, with reference to Formula 1, the Y group is cyclopropyl and the $X_1$ groups joint represent an oxo (=O) or a thione (=S) function, and where the radical $C(X_2X_2)$—W—$R_{14}$ represents an alkyl arylalkyl or heteroaryl group, preferably an alkyl group. The sequence of reactions, as illustrated in Reaction Scheme 2 gives rise to 6-substituted tetrahydroquinoline-2-one or 6-substituted tetrahydroquinoline-2-thione compounds. However a person of ordinary skill in synthetic organic chemistry can readily adapt these reactions for the preparation of 7-substituted tetrahydroquinoline-2-one or 7-substituted tetrahydroquinoline-2-thione compounds within the scope of this invention.

The starting compound in the sequence of reactions illustrated in Reaction Scheme 2 is 4-bromo aniline or a 4-bromo-aniline that is substituted with an $R_3$ group as that group is defined in connection with Formula 1. The starting 4-bromo aniline or a 4-bromo-aniline derivative (Formula 18) is available commercially or in accordance with prior art patent and scientific literature. In the synthesis of the presently preferred compounds of the invention the starting compound is simply 4-bromo-aniline. The 4-bromo-aniline derivative of Formula 18 is reacted with an aldehyde or ketone compound $X_2$—CO—$X_2$ and the resulting Schiff base is reduced with a suitable reducing agent, such as sodium borohydride ($NaBH_4$) to provide a 4-bromo-N-alkyl (or N-aryl)-aniline derivative of Formula 19. An example for the reagent $X_2$—CO—$X_2$ is acetone, which gives rise to the intermediate 4-bromo-N-(2-propyl)-aniline used in the synthesis of certain specific preferred compounds of the invention, and this type of reaction with acetone is described in J. Org. Chem., 1978, 4750–4758. The 4-bromo-N-alkyl-aniline derivatives of Formula 19 can also be obtained by alternative procedures, for example by alkylation or arylation of 4-bromo-aniline.

The 4-bromo-N-alkyl-aniline derivative of Formula 19 is thereafter reacted with a 3,3-dialkylacryloyl chloride of Formula 20 where $R_2$ is is defined as in connection with Formula 1; preferably $R_2$ is methyl. The result of this acylation reaction is a N-(4-bromophenyl)-N-(alkyl)-butenamide derivative of Formula 21. An example for the 3,3-dialkylacryloyl chloride reagent of Formula 20 is 3,3-dimethylacryloyl chloride that is used in the synthesis of certain specific preferred compounds of the invention. The butenamide derivative of Formula 21 is thereafter ring-closed under Friedel-Crafts like conditions (heating in the presence of $AlCl_3$) to provide a 6-bromo-4,4-dialkyl-1-(alkyl)-2-oxo-1,2,3,4-tetrahydroquinoline derivative of Formula 22. An actual example for the intermediate of Formula 22 that is utilized in the synthesis of certain preferred compounds of the invention is 6-bromo-4,4-dimethyl-1-(2-propyl)-2-oxo-1,2,3,4-tetrahydroquinoline. The Friedel Crafts-like ring closure reaction of the type utilized above is described in the chemical literature, for example in J. Med. Chem., 1997, 40, 3567–3583. Instead of the bromo intermediates 6-trifluoromethylsulphonyl-4,4-dialkylyl-1-(alkyl)-2-oxo-1,2,3,4-tetrahydroquinoline derivative analogs to the compounds of Formula 22 can also be obtained in accordance with synthetic methods described in the patent literature, or by such modifications of known synthetic methods that are readily apparent to those skilled in the art. See for example U.S. Pat. No. 5,739,338 (Scheme 7), the specifications of which are incorporated herein by reference. The trifluoromethylsulphonyl derivatives of this reference patent can also be converted to the boronic acid intermediates of Formula 23.

Referring still to Reaction Scheme 2, the 6-bromo-4,4dialkyl-1-(alkyl)-2-oxo-1,2,3,4-tetrahydroquinoline derivative of Formula 22 is reacted with trimethoxyboron ($(CH_3O)_3B$) to provide the 4,4-dialkyl-1-(alkyl)-2-oxo-1,2,3,4-tetrahydroquinoline boronic acid compounds of Formula 23. The reaction with trimethoxyboron is typically conducted in an aprotic ether type solvent, preferably diethyl ether or THF at low (−78 to −40° C.) temperature. The boronic acid derivatives of Formula 23 are thereafter reacted in an inert solvent, or solvent mixture, such as a mixture of toluene, methanol and water, with a 3-iodo-allyl alcohol derivative of Formula 24 in the presence of tetrakis (triphenylphosphine)palladium(0) catalyst at elevated (approx. 100° C.) temperature, in the presence of an acid acceptor. A specific example for the 3-iodo-allyl alcohol reagent of Formula 24 that is used in the synthesis of certain specific preferred compounds of the invention is 3-iodo-but-2-ene-1-ol ($R_1$ of Formula 24 is methyl). The products of the coupling reaction with the 3-iodo-allyl alcohol reagent of Formula 24 are 4,4-dialkyl-6-(3-hydroxy-1-allyl-prop-1-enyl)-2-oxo-1-(alkyl)-1,2,3,4-tetrahydroquinoline derivatives of Formula 25. The double bond in the butene moiety is in the cis orientation when the 3-iodo allylic alcohol derivative has the cis orientation. Compounds of trans orientation can also be obtained provided the orientation of the 3-iodo allylic alcohol reagent is trans. When, as in the below described specific example 3-iodo-but-2(Z)-ene-ol is used as the reagent of Formula 24, with the other preferred exemplary reagent, then the product is 4,4-dimethyl-6-(3-hydroxy-1-methyl-prop-1(Z)-enyl)-2-oxo-1-(2-propyl)-1,2,3,4-tetrahydroquoline.

The 4,4-dialkyl-6-(3-hydroxy-1-alkyl-prop-1-enyl)-2-oxo-1-(alkyl)-1,2,3,4-tetrahydroquinoline derivatives of Formula 25 are then converted to the corresponding cyclopropyl derivatives, 4,4-dialkyl-6-(3-hydroxy-1 ,2-methano-1-alkyl-propyl)-2-oxo-1-(alkyl)-1,2,3,4-tetrahydroquinolines of Formula 26. This "cyclopropylation" reaction employs the reagent diiodomethane in the presence of a suitable catalyst. The cyclopropylation reaction is usually conducted at cold temperature (−25° C.), in an inert solvent such as anhydrous dichloromethane, 1,2-dimethoxyethane or mixtures thereof, in an inert (argon) gas atmosphere. In the cyclopropylation reaction the orientation (cis or trans) of the double bond to which the methylene group is attached, is maintained, so that from a cis allylic alcohol of Formula 25 a cis cyclopropyl derivative of Formula 26 is obtained, whereas a trans allylic alcohol of Formula 25 yields a trans cyclopropyl derivative. A suitable catalyst for the cyclopropylation reaction is the presence of both mercury(II)chloride, and samarium. However, the presence of this catalytic mixture does not provide enantio selectivity for the resulting cyclopropyl derivatives. When enantio selectivity is desired, optically active tetramethyltartaramide catalyst, specifically (4S-trans)-2-butyl-N,N,N',N'-tetramethyl[1,3,2]dioxaborolane--[4,5]dicarboxamide, shown in Reaction Scheme 2, and diethyl zinc ($Et_2Zn$) are used as catalysts. This cyclopropylation reaction using optically active tetramethyltartaramide catalyst is in analogy to a similar reaction (performed on different materials) described in *Journal of Organic Chemistry* (1995) 60 1081–1083, and in *Tet. Lett.*, 1996, 37, 7925–7928.

The alcohols of Formula 26 can be resolved to provide an optically pure single enantiomer by reacting the alcohol with (1S)-camphanic chloride, isolating one pure diastereometric ester compound and thereafter saponifying the ester. This is indicated in the reaction scheme. A specific example of an alcohol intermediate that is obtained in optically pure form through the above-described process of resolution is 4,4-dimethyl-6-(3-hydroxy-1,2-methano-1-methyl-propyl)-2-oxo-1-(2-propyl)-1,2,3,4-tetrahydroquinoline which is used in the synthesis of specific preferred compounds of the invention.

In the next reaction step, and after resolution to a single chiral compound, if desired, the 4,4-dialkyl-6-(3-hydroxy-1,2-methano-1-alkyl-propyl)-2-oxo-1-(alkyl)-1,2,3,4-tetrahydroquinolines derivatives of Formula 26 are oxidized to the "aldehyde stage" to yield 4,4dialkyl-6-[(1S,2S)-3-oxo-1,2-methano-1-alkyl-propyl]-2-oxo-1-(alkyl)-1,2,3,4-tetrahydroquinoline derivatives of Formula 27. The reaction scheme illustrates this step on a single chiral compound. It will be recognized by those skilled in the art that several reagents are suitable for this oxidation step. The presently preferred reagents and conditions for this reaction include the use of methylene chloride as the solvent, and tetra-n-propyl ammonium perruthenate and N-methyl morpholine N-oxide as reagent and catalyst. The oxidation reaction is typically conducted at room temperature. Other suitable reagents for this oxidation reaction include, as it will be readily understood by those skilled in the art, pyridinium dichromate, oxalyl chloride and dimethylsulfoxide or trifluoroacetic anhydride and dimethylsulfoxide.

The 4,4-dialkyl-6-[(1S,2S)-3-oxo-1,2-methano-1-alkyl-propyl]-2-oxo-1-(alkyl)-1,2,3,4-tetrahydroquinoline derivatives-of Formula 27 are subsequently reacted with a diethylphosphono reagent. The diethylphosphono reagent shown in the reaction scheme for the present examples is ethyl diethylphosphono-3-methyl-2(E)-butenoate which can be obtained in accordance with the chemical literature (*J. Org. Chem.* 1974 39 p 821). The reaction with the diethylphosphono reagent is known in the art as the Horner Emmons reaction. It is conducted in the presence of strong base (such as n-butyl lithium) in an inert solvent, such as tetrahydrofuran, usually at low temperature (typically −78° C.) and results in the formation of a double bond to replace the oxo function of the reagent of Formula 27. The resulting products in this example, are 7-(4,4-dialkyl-2-oxo-1-(alkyl)-1,2,3,4-tetrahydro-quinolin-6-yl)-6,7-methano-3-methyl-2E,4E-dienoic acid ethyl ester derivatives of Formula 28. Instead of the diethylphosphono Horner Emmons reagent an analogous Wittig reagent can also be utilized in the coupling reaction. The structure of such a Wittig reagent will be readily apparent to those skilled in the art in light of the present disclosure. The herein described Horner Emmons coupling reaction typically provides as predominant product the isomer where the orientation about the newly formed double bond ($\blacktriangledown^4$ of the dienoic acid) is trans, and normally only this trans isomer, or predominantly the trans isomer is isolated from the reaction mixture. However, it is also possible to obtain a greater proportion of the corresponding cis isomer by adjusting conditions of the Horner Emmons reaction. The ester compounds of Formula 28 are readily saponified to give the free carboxylic acid derivatives of Formula 29. An example of an optically and sterochemically pure free carboxylic acid of the invention, within the scope of Formula 29 is (6S,7S)-7-(4,4-dimethyl-2-oxo-1-(2-propyl)-1,2,3,4-tetrahydro-quinolin-6-yl)-6,7-methano-3-methyl-octa-2E,4E-dienoic acid.

The 2-oxo function of the tetrahydroquinoline moiety of the compounds of Formula 28 is converted to a thione (═S) function by treatment of the compounds of Formula 28 with Lawesson's reagent [2,4-bis(4-methoxyphenyl)-1,3-dithia-2,4-diphosphetane-2,4-disulfide] by heating the ester in an inert solvent, such as toluene. The resulting 7-(4,4-dialkyl-1-(alkyl)-2-thioxo-1,2,3,4-tetrahydro-quinolin-6-yl)-6,7-methano-3-methyl-2E,4E-dienoic acid ethyl ester derivatives of Formula 30 are saponified to provide the free carboxylic acids of Formula 31. A specific example of an optically and sterochemically pure preferred 2-thioxo compound of the invention within the scope of Formula 31 is (6S,7S)-7-(4,4-dimethyl-1-(2-propyl)-2-thioxo-1,2,3,4-tetrahydro-quinolin-6-yl)-6,7-methano-3-methyl-octa-2E,4E-dienoic acid.

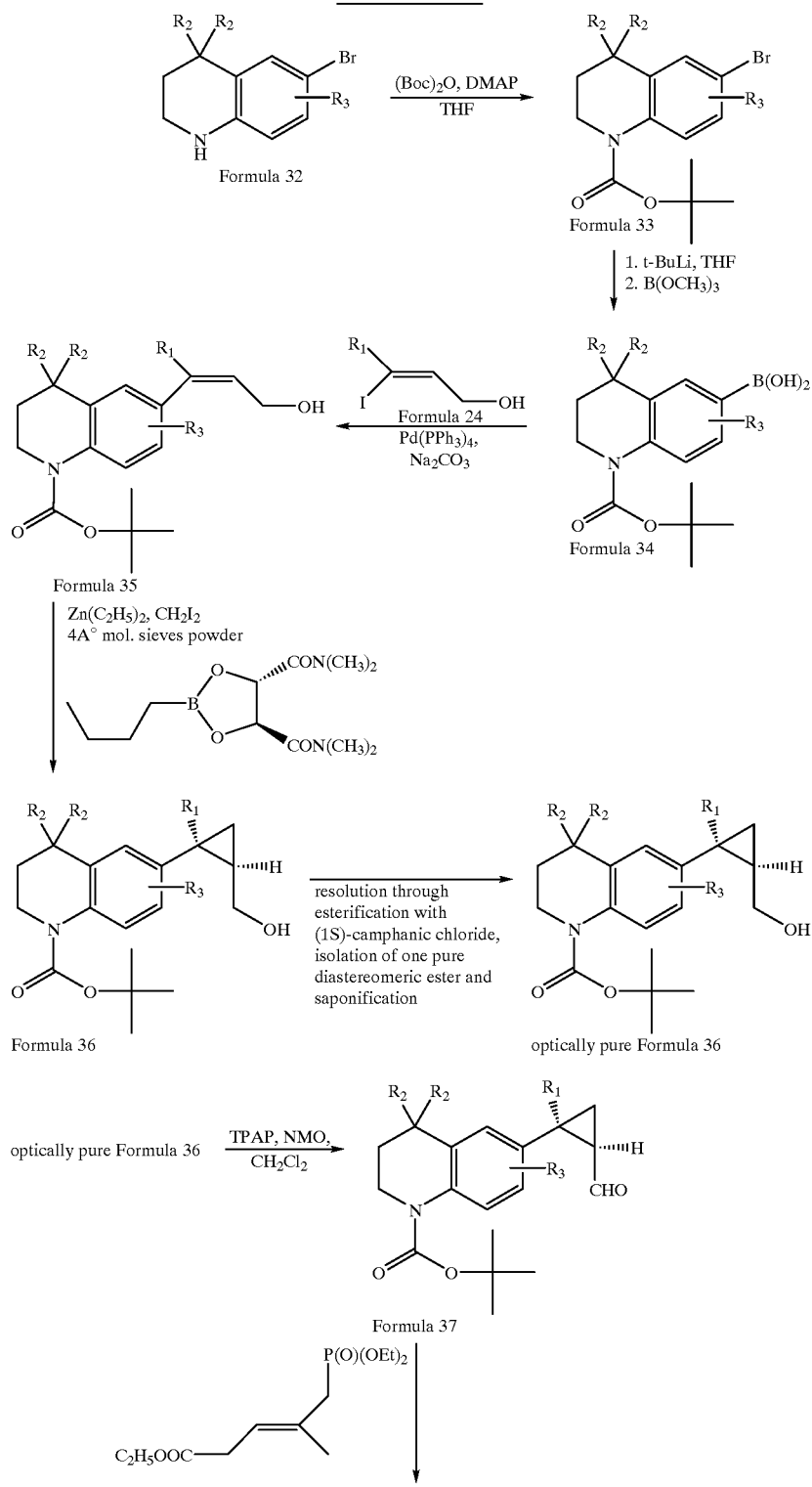

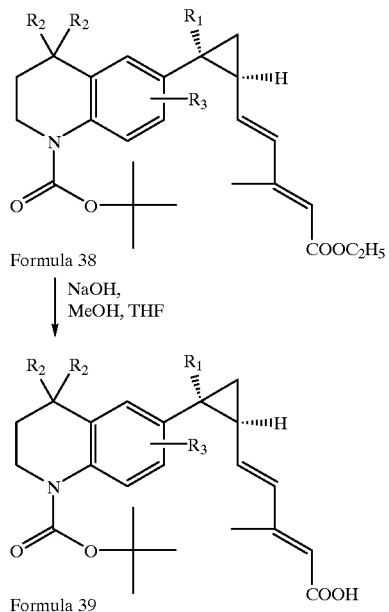

Formula 38

↓ NaOH, MeOH, THF

Formula 39

Reaction Scheme 3 discloses a synthetic route to another preferred class of compounds of the invention, where with reference to Formula 1 the Y group is cyclopropyl attached to the 6-position of the tetrahydroquinoline moiety, each of the $X_1$ groups is hydrogen, and the two $X_2$ groups jointly represent an oxo (=O) group. Thus, the sequence of reactions illustrated in Reaction Scheme 3 gives rise to 6-substituted tetrahydroquinoline derivatives also substituted in the N-1 position, where the N-1 substituent includes an electron withdrawing carbonyl group. The substituent of the N-1 position can be an oxycarbonyl group, as illustrated in this exemplary reaction scheme with tertiary-butyloxycarbonyl, or the substituent of the N-1 position can be an acyl group, such as for example acetyl or benzoyl.

The starting compound utilized in Reaction Scheme 3 is a 6-bromo-1,2,3,4-tetrahydroquinoline derivative of Formula 32 which bears the desired $R_2$ and $R_3$ substituents, or such precursors of these substituents which can be readily converted into the desired $R_2$ and $R_3$ groups. The compounds of Formula 32 can be obtained in accordance with prior art patent and scientific literature. In the synthesis of the presently preferred compounds of the invention the starting compound of Formula 32 is 6-bromo-4,4-dimethyl-1,2,3,4-tetrahydroquinoline, which can be obtained in accordance with the publication in *J. Med. Chem.*, 1997, 40 3567–3583 expressly incorporated herein by reference. The 6-bromo-4,4-dialkyl-1,2,3,4-tetrahydroquinoline derivative of Formula 32 is reacted with di-tert-butyl dicarbonate in the presence of an acid acceptor, such as 4-dimethylaminopyridine, to yield the 6-bromo-1-(tert-butyloxycarbonyl)-4,4-dialkyl-1,2,3,4-tetrahydroquinoline derivative of Formula 33. Alternatively, the 6-bromo-4,4-dialkyl-1,2,3,4-tetrahydroquinoline derivatives of Formula 32 can be acylated with any suitable acylating agent, such as an acid chloride, or reacted with other suitable agents to introduce an acyl group.

The 6-bromo-1-(tert-butyloxycarbonyl)-4,4-dialkyl-1,2, 3,4-tetrahydroquinoline derivatives of Formula 33 are then subjected to substantially the same sequence of reactions which are described for the analogous 6-bromo-4,4-dialkyl-1-(alkyl)-2-oxo-1,2,3,4-tetrahydroquinoline derivatives of Formula 22. For this reason, these analogous reaction steps are described only briefly. Thus, the 6-bromo-1-(tert-butyloxycarbonyl)-4,4-dialkyl-1,2,3,4-tetrahydroquinoline derivatives of Formula 33 are reacted with trimethoxyboron $(CH_3O)_3B$ to provide the 1-(tert-butyloxycarbonyl)-4,4-dialkyl-1,2,3,4-tetrahydroquinoline-6-boronic acid compounds of Formula 34. The boronic acid derivatives of Formula 34 are thereafter reacted with a 3-iodo-allyl alcohol derivative of Formula 24 in the presence of tetrakis (triphenylphosphine)palladium(0) catalyst and an acid acceptor. A specific example for the 3-iodo-allyl alcohol reagent of Formula 24 that is used in the synthesis of the herein described specific preferred compounds of the invention is 3-iodo-but-2-ene-1-ol ($R_1$ of Formula 24 is methyl). The products of the reaction with the 3-iodo-allyl alcohol reagent of Formula 24 are 1-(tert-butyloxycarbonyl)-4,4-dialkyl-6-(3-hydroxy-1-alkyl-prop-1-enyl)-1,2,3,4-tetrahydro-quinoline derivatives of Formula 35. When 3-iodo-but-2(Z)-ene-ol is used as the reagent of Formula 24 for the synthesis of a preferred embodiment, then the product is 1-(tert-butyloxycarbonyl)-4,4-dimethyl-6-(3-hydroxy-1-methyl-prop-1(Z)-enyl)-1,2,3,4-tetrahydro-quinoline.

The 1-(tert-butyloxycarbonyl)-4,4-dialkyl-6-(3-hydroxy-1-alkyl-prop-1-enyl)-1,2,3,4-tetrahydroquinoline derivatives of Formula 35 are then subjected to the "cyclopropylation" reaction which is described in detail in connection with Reaction Scheme 2. The products of the cyclopropylation reaction are 1-(tert-butyloxycarbonyl)-4,4-dialyl-6-[3-hydroxy-1,2-methano-1-alkyl-propyl]-1,2,3,4-tetrahydroquinoline derivatives of Formula 36. As in the process described in connection with Reaction Scheme 2, in this process also the alcohol of Formula 36 is preferably resolved into an optically pure single isomer through esterification with (1S)-camphanic chloride, subsequent isolation of a single diastereomer, followed by saponification of the camphanate ester. The optically pure single chiral alcohol of Formula 36 is then oxidized to the aldehyde stage, to give a 1-(tert-butyloxycarbonyl)-4,4-dialkyl-6-[3-oxo-1,2-methano-1-alky-propyl]-1,2,3,4-tetrahydroquinoline derivative of Formula 37. In the synthesis of the herein described preferred embodiment the product is the optically pure single enantiomer 1-(tert-butyloxycarbonyl)-4,4-dimethyl-6-[(1S,2S)-3-oxo-1,2-methano-1-methyl-propyl]-1,2,3,4-tetrahydroquinoline.

The aldehyde compounds of Formula 37 are then subjected to a Horner Emmons reaction with a diethylphosphono reagent such as ethyl diethylphosphono-3-methyl-2(E)-butenoate that is illustrated in the reaction scheme. The products of the Horner Emmons reaction with this reagent are (1-(tert-butyloxycarbonyl)-4,4-dialkyl-1,2,3,4-tetrahydroquinolin-6-yl)-6,7-methano-3-methyl-2E,4E-dienoic acid ester derivatives of Formula 38. These ester compounds are readily saponified by treatment with base, such as sodium hydroxide, to provide the free acids of Formula 39. The compounds of Formula 38 and of Formula 39 both are within the scope of Formula 1 and within the scope of the invention.

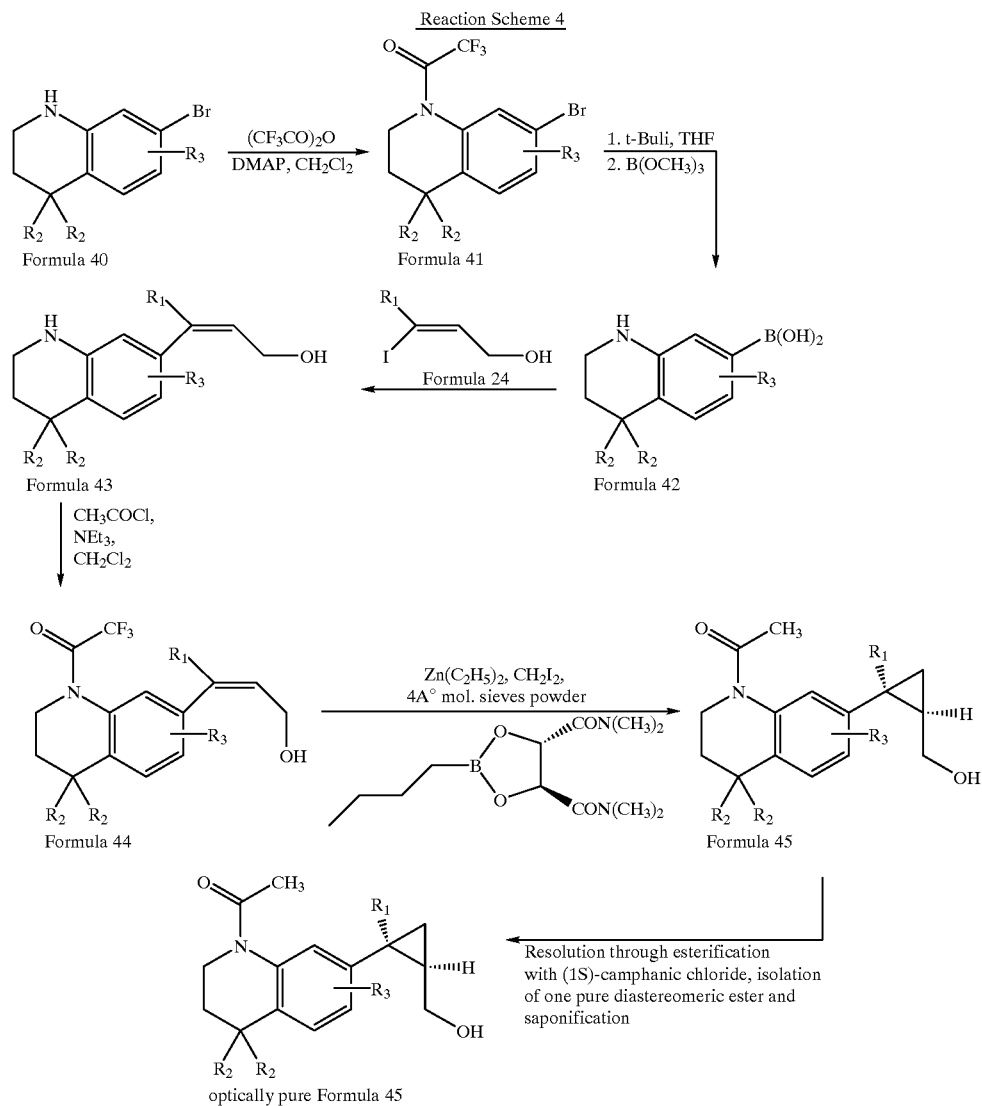

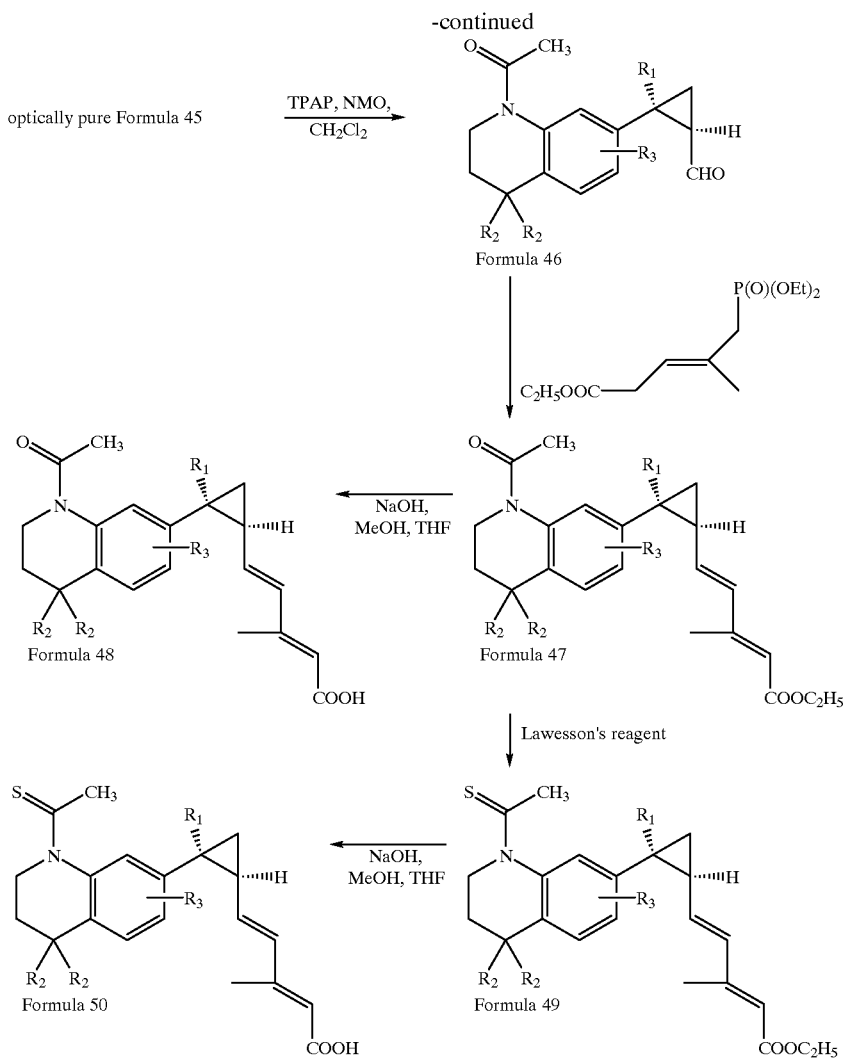

Reaction Scheme 4 discloses a synthetic route to still another preferred class of compounds of the invention, where with reference to Formula 1 the Y group is cyclopropyl attached to the 7-position of the tetrahydroquinoline moiety, each of the $X_1$ groups is hydrogen, and the two $X_2$ groups jointly represent an oxo (=O) or a thione (=S) group. The starting material in this reaction scheme is a 7-bromo-4,4-dialkyl-1,2,3,4-tetrahydroquinoline derivative of Formula 40, exemplified for the synthesis of the herein described actual preferred example by 7-bromo-4,4-dimethyl-1,2,3,4-tetrahydroquinoline. Compounds of Formula 40 are available in accordance with prior art patent and scientific literature (see J. Med Chem., 1997, 40, 3567–3583). The 7-bromo-4,4-dialkyl-1,2,3,4-tetrahydroquinoline derivatives of Formula 40 are reacted with trifluoroacetic anhydride in the presence of an acid acceptor such as 4-dimethylaminopyridine to provide N-trifluoroacetyl-7-bromo-4,4-dialkyl-1,2,3,4-tetrahydroquinoline derivatives of Formula 41. The bromo compounds of Formula 41 are reacted with trimethoxyboron $(CH_3O)_3B)$ in the presence of t-butyl lithium as described above in connection with Reaction Schemes 2 and 3. The reaction with trimethoxyboron removes the trifluoroacetyl blocking group and provides 4,4-dialkyl-1,2,3,4-tetrahydroquinoline-7-boronic acid derivatives of Formula 42.

The 4,4-dialkyl-1,2,3,4-tetrahydroquinoline-7-boronic acid derivatives of Formula 42 are thereafter reacted with a 3-iodo-allyl alcohol derivative of Formula 24, and specifically with 3-iodo-but-2-ene-1-ol, in the presence of tetrakis (triphenylphosphine)palladium(0) catalyst and an acid acceptor. The products of the reaction with the 3-iodo-allyl alcohol reagent of Formula 24 are 4,4-dialkyl-7-(3-hydroxy-1-alkyl-prop-1(Z)-enyl)-1,2,3,4-tetrahydroquinoline derivatives of Formula 43. An acyl group, exemplified in the reaction scheme by an acetyl group, is then introduced into the compounds of Formula 43 by treatment with a suitable acylating agent, such as an acid chloride or anhydride, to provide 1-acetyl-4,4-dialkyl-7-(3-hydroxy-1-alkyl-prop-1 (Z)-enyl)-1,2,3,4-tetrahydro-quinoline derivatives of Formula 44. In the synthesis of the preferred embodiment of this class of compounds of the invention the product of the acylation reaction is 1-acetyl-4,4-dimethyl-7-(3-hydroxy-1-methyl-prop-1(Z)-enyl)-1,2,3,4-tetrahydro-quinoline.

The 1-acetyl-4,4-dialkyl-7-(3-hydroxy-1-alyl-prop-1(Z)-enyl)-1,2,3,4-tetrahydro-quinoline derivatives of Formula 44 are then subjected to the cyclopropylation reaction described above. The cyclopropylation reaction is thereafter preferably followed by resolution to provide a single chiral alcohol of Formula 45. The alcohol of Formula 45 is then oxidized to aldehyde (Formula 46), and the aldehyde is subjected to a Horner Emmons reaction, to provide (1-acetyl-4,4-dialkyl-1,2,3,4-tetrahydro-quinolin-7-yl)-6,7-methano-3-methyl-2E,4E-dienoic acid ethyl ester derivatives of Formula 47. The esters of Formula 47 are saponified to provide the (1-acetyl-4,4-dialkyl-1,2,3,4-tetrahydro-quinolin-7-yl)-6,7-methano-3-methyl-2E,4E-dienoic acid derivatives of Formula 48. These reactions are carried out in substantially the same manner as the analogous reactions described above in connection with Reaction Schemes 2 and 3. The esters of Formula 47 and the acids of Formula 48 are within the scope of the invention.

The esters of Formula 47 are also reacted with Lawesson's reagent to provide compounds of the invention (Formula 49) where the two $X_2$ groups of Formula 1 jointly represent a thione (=S) function. The thio compounds of Formula 49 are also be saponified to provide the dienoic acid compounds of Formula 50 within the scope of the invention.

SPECIFIC EMBODIMENTS

4-Bromo-N-(2-propyl)-aniline

Compound 4

A solution of 4-bromoaniline 3 (8.6g, 50mmol) in a mixture of acetic acid (42 mL), acetone (30 mL), ethanol (50 mL) and water (125 mL) was treated with sodium acetate (13.6 g, 100 mmol) and cooled in an ice bath. Sodium borohydride (10 g, 0.37 mmol) was added in small portions over 3.5 hours while maintaining ice-bath temperature. The solution was then neutralized with 20 g of sodium hydroxide and extracted with ether (2×300 mL). The combined ether extract was dried over anhydrous sodium sulfate and the solvent was evaporated in vacuo. The residual oil was dissolved in dichloromethane (120 mL), dried over anhydrous sodium sulfate and the solvent evaporated in vacuo to give a quantitative yield of the title compound.
$^1$H-NMR (300 MHz, CDCl$_3$):d 1.20(d, J=6.27 Hz, 6H), 3.48(br s, 1H), 3.58(heptet, J=6.3 Hz, 1H), 6.46(d, J=8.7 Hz, 2H), 7.24(d, J=8.8 Hz, 2H).

N-(4-Bromophenyl)-N-(2-propyl)-3-methyl-2-butenamide

Compound 5

A solution of 3,3-dimethylacryloyl chloride (5.56 mL, 50 mmol) in 120 mL of chloroform was added to a solution of 4-bromo-N-(2-propyl)-aniline (Compound 4, 10.4 g, 48.5 mmol) in 400 mL of chloroform over 5 minutes. The reaction mixture was then refluxed overnight. After cooling to room temperature, the reaction mixture was washed with 5% HCl (1×150 mL), saturated, aqueous sodium bicarbonate (1×150 mL) and brine (1×150 mL). The organic phase was dried over anhydrous sodium sulfate and the solvent evaporated in vacuo to afford 13.8 g (96%) of the title compound as a brown solid.
$^1$H-NMR (300 MHz, CDCl$_3$): d 1.05(d, J=6.8 Hz, 6H), 1.63(s, 3H), 2.08(s, 3H), 4.98(m, 1H), 5.22(br s, 1H), 6.95(d, J=8.5 Hz, 2H), 7.51(d, J=8.6 Hz, 2H).

6-Bromo-4,4-dimethyl-1-(2-propyl)-2-oxo-1,2,3,4-tetrahydroquinoline

Compound 6

N-(4-Bromophenyl)-N-(2-propyl)-3-methyl-2-butenamide (Compound 5 13.8 g, 46 mmol) was heated at 140° C. until it melted and aluminum chloride (9.86 g, 74 mmol) was added in portions over 0.5 hours. The reaction mixture was stirred for 0.5 hours at 140° C. and then cooled to room temperature. Ice was added cautiously to the solid, followed by ~200 mL of ice water. The reaction mixture was then extracted with ether (1×300 mL) and washed with saturated, aqueous sodium bicarbonate (1×150 mL) and brine (1×150 mL). The organic phase was dried over anhydrous sodium sulfate and the solvent evaporated in vacuo to yield a brown oil which was purified by flash column chromatography on silica gel (230–400 mesh) to afford 12.7 g of the title compound as an oil (94%). $^1$H-NMR (300 MHz, CDCl$_3$):d 1.27(s, 6H), 1.51(d, J=7.0 Hz, 6H), 2.40(s, 2H), 4.68(heptet, J=7.0 Hz, 1H), 7.00(d, J=8.7 Hz, 1H), 7.32(dd, J=8,6,2,2 Hz, 1H), 7.36(d, J=2.3 Hz, 1H).

4,4-Dimethyl-2-oxo-1-(2-propyl)-1,2,3,4-tetrahydroquinoline-6-boronic acid

Compound 7

To a stirred, cooled (−78° C.) solution of 6-bromo-4,4-dimethyl-2-oxo-1-(2-propyl)-1,2,3,4-tetrahydroquinoline (Compound 6 5.9 g, 20 mmol) in anhydrous tetrahydrofuran (100 mL) under argon, 24 mL (40.6 mmol) of a 1.7M solution of t-butyl lithium in pentane was added over 5 minutes, and the solution turned deep red in color. After stirring at (−78° C.) for 1 hour, trimethyl borate ( 4.6 mL, 40.8 mmol) was added (which caused disappearance of the red color) and the reaction mixture was stirred from −78° C. to −40° C. over 2 hours and at ambient temperature for 15 minutes. The reaction was quenched by adding 50 mL of saturated, aqueous ammonium chloride solution and extracted with ether (1×100 mL). The organic phase was dried over anhydrous sodium sulfate and the solvent evaporated in vacuo to give a yellow oil. Treatment with 40 mL of 1:1 hexane: dichloromethane led to the precipitation of a white solid which was removed by filtration and dried to yield 1.2 g of the title compound as a white solid (23%).
$^1$H-NMR (300 MHz, CD$_3$COCD$_3$):d 0.61(s, 6H), 0.85(d, J=7.0 Hz, 6H), 1.68(s, 2H), 3.99(heptet, J=7.0 Hz, 1H), 6.53(d, J=8.2 Hz, 1I), 6.66(s, 2H), 7.10(dd, J=8.2, 1.5 Hz, 1H), 7.19(d, J=1.5 Hz, 1H).

4,4-dimethyl-6-(3-hydroxy-1-methyl-prop-1(Z)-enyl)-2-oxo-1-(2-propyl)-1,2,3,4-tetrahydroquinoline Compound 9

A solution of 4,4-dimethyl-2-oxo-1-(2-propyl)-1,2,3,4-tetrahydroquinoline-6-boronic acid (Compound 7 0.54 g, 2.08 mmol) and 3-iodo-but-2(Z)-ene-ol (Compound 8 0.5 g, 2.5 mmol) in a mixture of methanol (8 mL), toluene (16 mL) and water (4 mL) was treated with sodium carbonate (0.96 g, 9.2 mmol) and tetrakis(triphenylphosphine)palladium(0), degassed with argon for 5 minutes, and heated at 100° C. overnight. The reaction mixture was cooled to ambient temperature, all volatiles were removed by distillation in vacuo and the residue was diluted with water (30 mL) and extracted with ether (2×40 mL). The combined organic extract was dried over anhydrous sodium sulfate and the solvent was evaporated in vacuo to give an oily residue which was purified by flash column chromatography over silica gel (230–400 mesh) using 30% ethyl acetate in hexane as the eluent to provide 0.43 g (72%) of the title compound as a pale brown oil. $^1$H-NMR (300 MHz, CDCl$_3$):d 1.26(s, 6H), 1.53(d, J=7.1 Hz, 6H), 2.08(s, 3H), 2.41(d, J=1.3 Hz, 2H), 4.11(dd, J=6.2, 1.1 Hz, 2H), 4.68(heptet, J=6.8 Hz, 1H), 5.71(t, J=7.1 Hz, 1H), 7.04–7.25(m, 3H).

4,4-Dimethyl-6-[(1S,2S)-3-hydroxy-1,2-methano-1-methyl-propyl]-2-oxo-1-(2-propyl)-1,2,3,4-tetrahydroquinoline Compound 11

To a stirred, cooled (−25° C.) solution of diethyl zinc in anhydrous dichloromethane ( 9.06 mL, 16.4 mmol) under argon, 1,2-dimethoxyethane (1.7 mL, 16.4 mmol) was added over 2 minutes followed by diiodomethane (2.7 mL, 32.8 mmol) at such a rate that the temperature of the cooling bath did not increase above −20° C. After the addition was complete, the reaction mixture was stirred for 5 minutes and then cannulated into a cooled (−25° C.), stirred solution of 4,4-dimethyl-6-(3-hydroxy-1-methyl-prop-1(Z)-enyl)-2-oxo-1-(2-propyl)-1,2,3,4-tetrahydroquinoline (Compound 9 0.43 g, 1.5 mmol), 4A° molecular sieves powder (0.5 g) and (4S-trans)-2-butyl-N,N,N',N'-tetramethyl[1,3,2] dioxaborolane-[4,5]dicarboxamide (Compound 10) in 10 mL of anhydrous dichloromethane over 5 minutes. The slurry was stirred at −25+ C. for 1.5 hour, at −15° C. for 3 hours and at 0° C. for 3 hours. The reaction was quenched with 20 mL of saturated, aqueous ammonium chloride solution and extracted with dichloromethane (2×35 mL). The combined organic extract was dried over anhydrous sodium sulfate and the solvent evaporated to give a residue which on purification by flash column chromatography on silica gel (230–400 mesh) using 30% ethyl acetate in hexane as the eluent provided 0.41 g (91%) of the title compound as a pale yellow, viscous oil.

$^1$H-NMR (300 MHz, CDCl$_3$):d 0.78–0.86(m, 2H), 1.20–1.30(m, 1H), 1.27(s, 6H), 1.39(s, 3H), 1.53(d, J=7.0 Hz, 6H), 2.40(s, 2H), 3.25(dq, J=11.4 Hz, 2H), 4.64(heptet, J=7.0 Hz, 1H), 7.04(d, J=8.4 Hz, 1H), 7.17(dd, J=8.3, 2.0 Hz, 1H), 7.22(d, J=2.0 Hz, 1H).

(1S)-Camphanate ester of 4,4-dimethyl-6-[(1S,2S)-3-hydroxy-1,2-methano-1-methyl-propyl]-2-oxo-1-(2-propyl-1,2,3,4-tetrahydroquinoline Compound 12

A stirred, cooled (ice-bath) solution of 4,4-dimethyl-6-(3-hydroxy-1 ,2-methano-1-methyl-propyl)-2-oxo-1-(2-propyl)-1,2,3,4-tetrahydroquinoline (Compound 11 0.41 g, 1.37 mmol) in anhydrous dichloromethane (10 mL) was treated with triethylamine (0.6 mL, 4.11 mmol) followed by (1S)-camphanic chloride (0.48 g, 2.2 mmol) under argon. The solution was allowed to warm to ambient temperature and stirred overnight. The reaction mixture was diluted with dichloromethane (50 mL) and washed with water (1×20 mL), dried over anhydrous sodium sulfate and evaporated in vacuo to a viscous oil. Flash column chromatography on silica gel (230–400 mesh) using 22% ethyl acetate in hexane as the eluent provided 0.62 g (94%) of the title compound as a white foam. The product was further purified by preparative reverse phase HPLC to eliminate the minor isomer formed during the cyclopropylation.

$^1$H-NMR (300 MHz, CDCl$_3$):d 0.88–0.95(m, 2H), 0.98(s, 3H), 1.05(s, 3H), 1.13(s, 3H), 1.28(s, 3H), 1.30(s, 3H), 1.35–1.45(m, 1H), 1.39(s, 3H), 1.54(d, J=7.0 Hz, 6H), 1.65–1.75(m, 1H), 1.88–2.04(m. 2H), 2.35–2.45(m, 1H), 2.41(s, 2H), 3.87(d, J=7.5 Hz, 2H), 4.65(heptet, J=7.0 Hz, 1H), 7.04(d, J=8.4 Hz, 1H), 7.15(dd, J=8.3, 2.0 Hz, 1H), 7.19(d, J=2.0 Hz, 1H).

4,4-Dimethyl-6-[(1S,2S)-3-hydroxy-1,2-methano-1-methyl-propyl]-2-oxo-1-(2-propyl)-1,2,3,4-tetrahydroquinoline Compound 13

A solution of the (1S)-camphanate ester of 4,4-dimethyl-6-(3-hydroxy-1,2-methano-1-methyl-propyl)-2-oxo-1-(2-propyl)-1,2,3,4-tetrahydroquinoline Compound 12 0.62 g, 1.29 mmol) in 10 mL of 1:1 methanol:tetrahydrofuran mixture was treated with a solution of lithium hydroxide monohydrate (0.2 g, 4.76 mmol) in water (1.2 mL) and the resulting clear, homogenous solution was stirred at ambient temperature for 1 hour. The volatiles were removed by distillation in vacuo and the residue was diluted with water (30 mL) and extracted with ether (2×30 mL). The combined organic extract was dried over anhydrous magnesium sulfate, filtered and evaporated in vacuo to afford 0.38 g (98%) of the title compound as a colorless, viscous oil.

$^1$H-NMR (300 MHz, CDCl$_3$):d 0.78–0.86(m, 2H), 1.20–1.30(m, 1H), 1.27(s, 6H), 1.39(s, 3H), 1.53(d, J=7.0 Hz, 6H), 2.40(s, 2H), 3.25(dq, J=11.4 Hz, 2H), 4.64(heptet, J=7.0 Hz, 1H), 7.04(d, J=8.4 Hz, 1H), 7.17(dd, J=8.3, 2.0 Hz, 1H), 7.22(d, J=2.0 Hz, 1H).

4,4-Dimethyl-6-[(1S,2S)-3-oxo-1,2-methano-1-methyl-propyl]-2-oxo-1-(2-propyl)-1,2,3,4-tetrahydroquinoline Compound 14

A solution of 4,4-dimethyl-6-[(1S,2S)-3-hydroxy-1,2-methano-1-methyl-propyl]-2-oxo-1-(2-propyl)-1,2,3,4-tetrahydroquinoline (Compound 13 0.1 g, 0.33 mmol) in dichloromethane (5 mL) and acetonitrile (1 mL) was treated sequentially with 4A° molecular sieves powder (0.15 g), tetra-n-propylammoniumperruthenate (0.025 g) and N-methylmorpholine-N-oxide (0.1 g, 0.85 mmol) and the resulting slurry was stirred at ambient temperature for 1 hour. The reaction mixture was diluted with 5 mL of hexane and subjected to flash column chromatography on silica gel using 20% ethylacetate in hexane as the eluent to afford 0.07 g (71%) of the title compound as a viscous oil.

$^1$H-NMR (300 MHz, CDCl$_3$):d 1.25(s, 3H), 1.27(s, 3H), 1.43(dd, J=8.0 Hz, 1H), 1.47(s, 3H), 1.52(d, J=7.0 Hz, 6H), 1.87(t, J=5.1 Hz, 1H), 1.94–2.04(m, 1H), 2.40(s, 2H), 4.64 (heptet, J=7.0 Hz, 1H), 7.04(d, J=8.4 Hz, 1H), 7.16(dd, J=8.4, 2.1 Hz, 1H), 7.19(d, J=2.1 Hz, 1H), 8.47(d, J=7.0 Hz, 1H).

(6S,7S)-7-(4,4-Dimethyl-2-oxo-1-(2-propyl)-1,2,3,4-tetrahydroquinolin-6-yl)-6,7-methano-3-methyl-octa-2E,4E-dienoic acid ethyl ester Compound 15

A stirred, cooled (−78° C.) solution of methyl-3-methyl-4-diethylphosphonocrotonate (0.58 g, 2.2 mmol) in 5 mL of anhydrous tetrahydrofuran and 1 mL of 1,3-dimethyl-3,4,5,6-tetrahydro-2(1H)-pyrimidinone (DMPU) was treated with 1.6M solution of n-butyllithium in hexanes (1.4 mL, 2.2 mmol). After 10 minutes, a solution of 4,4-dimethyl-6-[(1S, 2S)-3-oxo-1,2-methano-1-methyl-propyl]-2-oxo-1-(2-propyl)-1,2,3,4-tetrahydroquinoline (Compound 14 0.07 g, 0.22 mmol) in tetrahydrofuran (2 mL) was cannulated and the reaction mixture was allowed to warm to −20° C. over 1 hour. It was then quenched with 15 mL of saturated, aqueous solution of ammonium chloride and extracted with ether (2×20 mL), and the combined organic extract was dried over anhydrous sodium sulfate and the solvent evaporated in vacuo to give a pale yellow oil. Flash column chromatography on silica gel (230–400 mesh) using 10% ethyl acetate in hexane as the eluent afforded an oil contaminated with 1.2% of the 4Z isomer. The latter mixture was purified by preparative reverse phase HPLC to afford 0.081 g of the title compound.

$^1$H-NMR (300 MHz, CDCl$_3$):d 1.12(t, J=5.0 Hz, 1H), 1.19–1.30(m, 4H), 1.23(s, 3H), 1.27(s, 3H), 1.43(s, 3H), 1.53(dd, J=7.0, 2.3 Hz, 6H), 1.75(m, 1H), 2.00(s, 3H), 2.40(Abq, J=18 Hz, 2H), 4.14(q, J=7.3 Hz, 2H), 4.68(heptet, J=7.0 Hz, 1H), 5.21(dd, J=9.9, 15.5 Hz, 1H), 5.64(s, 1H), 6.19(d, J=15.6 Hz, 1H), 7.05(d, J=8.7 Hz, 1H), 7.09–7.12 (overlapping dd, d, 2H).

(6S,7S)-7-(4,4-Dimethyl-2-oxo-1-(2-propyl)-1,2,3,4-tetrahydroquinolin-6-yl)-6,7-methano-3-methyl-octa-2E,4E-dienoic acid

Compound 1

A solution of (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid ethyl ester (Compound 15 0.03 g, 0.074 mmol) in 3 mL of 1:1 methanol:tetrahydrofuran was treated with 1 mL of 1M aqueous sodium hydroxide and the resulting clear, homogeneous solution was heated at 60° C. overnight The reaction mixture was cooled to room temperature and the volatiles were removed by distillation in vacuo. The residue was diluted with 10 mL of water, neutralized with hydrochloric acid and extracted with ether (2×15 mL). The combined organic extract was dried over anhydrous sodium sulfate and evaporated in vacuo to an oily residue which was purified by flash chromatography on silica gel (230–400 mesh) using 30% ethyl acetate in hexane as the eluent to afford 0.017 g (61%) of the title compound as a foamy solid.
$^1$H-NMR (300 MHz, CDCl$_3$):d 1.13(t, J=4.9 Hz, 1H), 1.19–1.29(m,1H), 1.23(s, 3H), 1.27(s, 3H), 1.43(s, 3H), 1.53(dd, J=7.2, 2.1 Hz, 6H), 1.73–1.81(m, 1H), 2.00(s, 3H), 2.40(Abq, J=18 Hz, 2H), 4.68(heptet, J=6.9 Hz, 1H), 5.26 (dd, J=10.7, 15.6 Hz, 1H), 5.66(s, 1H), 6.23(d, J=15.4 Hz, 1H), 7.04–7.12(overlapping dd, d, d, 3H).

(6S,7S)-7-(4,4-Dimethyl-1-(2-propyl)-2-thioxo-1,2,3,4-tetrahydroquinolin-6-yl)-6,7-methano-3-methyl-octa-2E,4E-dienoic acid ethyl ester

Compound 16

A solution of (6S,7S)-7-(4,4-Dimethyl-2-oxo-1-(2-propyl)-1,2,3,4-tetrahydroquinolin-6-yl)-6,7-methano-3-methyl-octa-2E,4E-dienoic acid ethyl ester (Compound 15 0.012 g, 0.03 mmol) in anhydrous toluene (1 mL) was treated with Lawesson's reagent (0.02 g, 0.049 mmol) under argon and heated at 85° C. for 1 hour. The reaction mixture was then cooled and subjected to flash column chromatography on silica gel using 10% ethyl acetate in hexane as the eluent to afford an oil that contained 9:1 ratio of the 4E and 4Z isomers which was further purified by reverse phase HPLC to provide 0.0045 g (36%) of the title compound as an oil.
$^1$H-NMR (300 MHz, CDCl$_3$):d 1.13–1.25(m, 8H),1.29 (t, J=7.1 Hz, 3H 1.44(s, 3H), 1.49(d, J=7.2 Hz, 3H), 1.55(d, J=7.2 Hz, 3H), 1.73–1.81(m, 1H), 1.97(s, 3H), 2.96(Abq, J=24 Hz, 2H), 4.14(q, J=7.2 Hz, 2H), 5.15(dd, J=9.9, 15.5 Hz, 1H), 5.63(s, 1H), 6.18(d, J=15.5 Hz, 1H), 6.23(heptet, J=7.1 Hz, 1H), 7.1(d, J=8.4 Hz, 1H), 7.13(s, 1H), 7.27(d, J=8.4 Hz, 1H).

(6S,7S)-7-(4,4-Dimethyl-1-(2-propyl)-2-thioxo-1,2,3,4-tetrahydroquinolin-6-yl)-6,7-methano-3-methyl-octa-2E,4E-dienoic acid

Compound 2

(6S,7S)-7-(4,4-Dimethyl-1-(2-propyl)-2-thioxo-1,2,3,4-tetrahydroquinolin-6-yl)-6,7-methano-3-methyl-octa-2E,4E-dienoic acid ethyl ester (Compound 16 0.0045 g, 0.01 mmol) was hydrolyzed substantially in accordance with the procedure described for the hydrolysis of (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid ethyl ester (Compound 15), to yield 0.0026 g of the title compound as a pale yellow solid (66%).
$^1$H-NMR (300 MHz, CDCl$_3$):d 1.12–1.36(m, 8H), 1.44(s, 3H), 1.49(d, J=7.2 Hz, 3H), 1.52(d, J=7.2 Hz, 3H), 1.74–1.80(m, 1H), 1.97(s, 3H), 2.95(Abq, J24.7 Hz, 2H), 5.20(dd, J9.9, 15.4 Hz, 1H), 5.65(s, 1H), 1s 6.21(d, J15.5 Hz, 1H), 6.18–6.24(m, 1H), 7.11(dd, J=8.4, 2.1 Hz, 1H), 7.15(d, J=2.1 Hz, 1H), 7.27(d, J=8.0 Hz, 1H).

6-Bromo-1-(tert-butyloxycarbonal)-4,4-dimethyl-1,2,3,4-tetrahydroquinoline

Compound 19

A solution of 6-bromo-4,4-dimethyl-1,2,3,4-tetrahydroquinoline (Compound 18 2.08 g, 8.6 mmol) in 16 mL of anhydrous tetrahydrofuran was treated sequentially with 4-dimethylaminopyridine (1.6 g, 12.9 mmol) and di-tert-butyl-dicarbonate (2.3 g, 10.3 mmol) and the deep yellow reaction mixture was stirred overnight at room temperature. During this time the reaction proceeded to partial completion only. The volatiles were removed by distillation in vacuo and the residue was diluted with water (20 mL) and extracted with ether (2×25 mL). The combined organic extract was dried over anhydrous sodium sulfate and the solvent evaporated to yield a residue which on chromatography provided the title compound (0.38 g, 13%) as a pale yellow oil.
$^1$H-NMR (300 MHz, CDCl$_3$):d 1.28(s, 6H), 1.51(s, 9H), 1.72(t, J=6.3 Hz, 2H), 3.71(t, J=6.2 Hz, 2H), 7.22(dd, J=8.8, 2.1 Hz, 1H), 7.37(d, J=2.5 Hz, 1H), 7.53(d, J=8.8 Hz, 1H).

1-(tert-Butyloxycarbonyl)-4,4-dimethyl-1,2,3,4-tetrahydroquinoline-6-boronic acid

Compound 20

6-Bromo-1-(tert-butyloxycarbonyl)-4,4-dimethyl-1,2,3,4-tetrahydroquinoline (Compound 19 0.79 g, 2.32 mmol) was converted to the title compound (yield of crude product 0.73 g) in analogy to the procedure for the preparation of 4,4-dimethyl-2-oxo-1-(2-propyl)-1,2,3,4-tetrahydroquinoline-6-boronic acid (Compound 7). The crude product was used in the next step without further purification.

1-(tert-Butyloxycarbonyl)-4,4-dimethyl-6-(3-hydroxy-1-methyl-prop-1(Z)-enyl)-1,2,3,4-tetrahyhydroquinoline

Compound 21

1-(tert-Butyloxycarbonyl)-4,4-dimethyl-1,2,3,4-tetrahydroquinoline-6-boronic acid (Compound 20 0.73 g crude, ~2 mmol) was converted into the title compound (0.44 g, overall yield for two steps 57%) in analogy to the procedure for the preparation of 4,4-dimethyl-6-(3-hydroxy-1-methyl-prop-1(Z)-enyl)-2-oxo-1-(2-propyl)-1,2,3,4-tetrahydroquinoline (Compound 9).
$^1$H-NMR (300 MHz, CDCl$_3$):d 1.25(s, 6H), 1.51(s, 9H), 1.73(t, J=6.1 Hz, 2H), 2.05(s, 3H), 2.19(br s, 1H), 3.72(t, J=6.0 Hz, 2H), 4.08(d, J=7.1 Hz, 2H), 5.65(t, 6.9 Hz, 1H), 6.94(dd, J=8.6, 2.1 Hz, 1H), 7.08(d, J=2.1 Hz, 1H), 7.59(d, J=8.5 Hz, 1H).

1-(tert-Butyloxycarbonyl)-4,4-dimethyl-6-[(1S,2S)-3-hydroxy-1,2-methano-1-methyl-propyl]-1,2,3,4-tetrahydroquinoline

Compound 22

1-(tert-Butyloxycarbonyl)-4,4-dimethyl-6-(3-hydroxy-1-methyl-prop-1(Z)-enyl)-1,2,3,4-tetrahydroquinoline (Compound 21 0.44 g, 1.33 mmol) was converted into the title compound (0.3 g, 65%) as a pale yellow, viscous oil in analogy to the procedure for the preparation of 4,4-dimethyl-6-[(1S,2S)-3-hydroxy-1,2-methano-1-methyl-propyl]-2-oxo-1-(2-propyl)-1,2,3,4-tetrahydroquinoline (Compound 11).

$^1$H-NMR (300 MHz, CDCl$_3$):d 0.75(dd, J=8.3, 4.8 Hz, 1H), 0.79(t, J=5.1 Hz, 1H), 1.19–1.26(m, 1H), 1.27(s, 6H), 1.35 (s, 3H), 1.50(s, 9H), 1.71(t, J=6.0 Hz, 2H), 3.20(d, J=7.2 Hz, 2H), 3.69(t, J=6.0 Hz, 2H), 7.04(dd, J=8.5, 2.1 Hz, 1H), 7.208(d, J=2.1 Hz, 1H), 7.55(d, J=8.4 Hz, 1H).

(1S)-Camphanate ester of 1-(tert-butyloxycarbonyl)-4,4-dimethyl-6-[(1S,2S)-3-hydroxy-1,2-methano-1-methyl-propyl]-1,2,3,4-tetrahydroquinoline Compound 23

1-(tert-Butyloxycarbonyl)-4,4-dimethyl-6-[(1S,2S)-3-hydroxy-1,2-methano-1-methyl-propyl]-1,2,3,4-tetrahydroquinoline (Compound 22 0.3 g, 0.87 mmol) was converted to the title compound (0.41 g, 92%) in analogy to the procedure for the preparation of (1S)-camphanate ester of 4,4-dimethyl-6-[(1S,2S)-3-hydroxy-1,2-methano-1-methyl-propyl]-2-oxo-1-(2-propyl)-1,2,3,4-tetrahydroquinoline (Compound 12). The title compound was purified on a preparative reverse phase HPLC column using 12% water in acetonitrile as the mobile phase.

$^1$H-NMR (300 MHz, CDCl$_3$):d 0.84-0.55(m, 2H), 0.978(s, 3H), 1.04(s, 3H), 1.12(s, 3H), 1.28(s, 3H), 1.29(s, 3H), 1.28–1.32(m, 1H), 1.36(s, 3H), 1.52(s, 9H), 1.61–1.69(m, 1H), 1.73(t, J=6.0 Hz, 2H), 1.85–2.08(m. 2H), 2.35–2.45(m, 1H), 3.68–3.80(m, 3H), 3.95(dd, J=11.5 Hz, 2H), 7.04(dd, J=8.4, 1.9 Hz, 1H), 7.18(d, J=1.9 Hz, 1H), 7.57(d, J=8.6 Hz, 1H).

1-(tert-Butyloxycarbonyl)-4,4-dimethyl-6-[(1S,2S)-3-hydroxy-1,2-methano-1-methyl-propyl]-1,2,3,4-tetrahydroquinoline Compound 22

(1S)-Camphanate ester of 1-(tert-butyloxycarbonyl)-4,4dimethyl-6-[(1S,2S)-3-hydroxy-1,2-methano-1-methyl-propyl]-1,2,3,4-tetrahydroquinoline (Compound 23 0.4 g, 0.8 mmol) was hydrolyzed to the title compound (0.27 g, 91%) in analogy to the procedure for the preparation of 4,4-dimethyl-6-[(1S,2S)-3-hydroxy-1,2-methano-1-methyl-propyl]-2-oxo-1-(2-propyl)-1,2,3,4-tetrahydroquinoline (Compound 13).

$^1$H-NMR (300 MHz, CDCl$_3$):d 0.75(dd, J=8.3, 4.8 Hz, 1H), 0.79(t, J=5.1 Hz, 1H), 1.19–1.26(m, 1H), 1.27(s, 6H), 1.35 (s, 3H), 1.50(s, 9H), 1.71(t, J=6.0 Hz, 2H), 3.20(d, J=7.2 Hz, 2H), 3.69(t, J=6.0 Hz, 2H), 7.04(dd, J=8.5, 2.1 Hz, 1H), 7.21(d, J=2.1 Hz, 1H), 7.55(d, J=8.4 Hz, 1H).

1-(tert-Butyloxycarbonyl)-4,4-dimethyl-6-[(1S,2S)-3-oxo-1,2-methano-1-methyl-propyl]-1,2,3,4-tetrahydroquinoline Compound 24

1-(tert-Butyloxycarbonyl)-4,4-dimethyl-6-[(1S,2S)-3-hydroxy-1,2-methano-1-methyl-propyl]-1,2,3,4-tetrahydroquinoline (Compound 23 0.27 g, 0.73 mmol) was oxidized to give the title compound (0.23 g, 92%) in analogy to the procedure for the preparation of 4,4-dimethyl-6-[(1S,2S)-3-oxo-1,2-methano-1-methyl-propyl]-2-oxo-1-(2-propyl)-1,2,3,4-tetrahydroquinoline (Compound 14).

$^1$H-NMR (300 MHz, CDCl$_3$):d 1.24(s, 3H), 1.26(s, 3H), 1.38(dd, J=7.9 Hz, 1H), 1.12(s, 3H),1.50(s, 9H), 1.70(t, J=6.1 Hz, 1H), 1.83(t, J=4.9 Hz, 1H),1.86–1.92(m, 1H), 3.69(t, J=5.9 Hz, 1H), 7.06(dd, J=8.6, 2.1 Hz, 1H), 7.18(d, J=2.1 Hz, 1H), 7.58(d, J=8.6 Hz, 1H), 8.39(d, J=7.0 Hz, 1H).

(6S ,7S) -7-(1-(tert-Butyloxycarbonyl)-4,4-dimethyl 1,2,3,4-tetrahydroquinolin-6-yl)-6,7-methano-3-methyl-octa-2E,4E-dienoic acid ethyl ester Compound 25

1-(tert-Butyloxycarbonyl)-4,4-dimethyl-6-[(1S,2S)-3-oxo-1,2-methano-1-methyl-propyl]-1,2,3,4-tetrahydroquinoline (Compound 24 0.23 g, 0.67 mmol) was converted into the title compound (0.26 g, 85%) in analogy to the procedure for the preparation of (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid ethyl ester (Compound 15). The crude product was purified on a preparative reverse phase HPLC column to remove the 3E isomer which was formed in minor amount (<1%).

$^1$H-NMR (300 MHz, CDCl$_3$):d 1.09 (t, J=5.0 Hz,1H), 1.17–1.35(m,10H), 1.40(s, 3H), 1.52(s, 9H), 1.69–1.75(m, 3H), 1.99(s, 3H), 3.65–3.79(m, 2H), 4.16(q, J=7.1 Hz, 2H), 5.24(dd, J=10.0, 15.4 Hz, 1H), 5.63(s, 1H), 6.19(d, J=15.5 Hz, 1H), 7.03(dd, J=8.4, 2.1 Hz, 1H), 7.13(d, J=2.1 Hz, 1H), 7.57(d, J=8.4 Hz, 1H).

(6S,7S)-7-(1-tert-Butyloxycarbonyl)-4,4-dimethyl -1,2,3,4-tetrahydroquinolin-6-yl)-6,7-methano-3-methyl-octa-2E,4E-dienoic acid Compound 17

(6S,7S)-7-(1-(tert-Butyloxycarbonyl)-4,4-dimethyl-1,2,3,4-tetrahydroquinolin-6-yl)-6,7-methano-3-methyl-octa-2E,4E-dienoic acid ethyl ester (Compound 25 0.02 g, 0.04 mmol) was hydrolyzed to the title compound (0.015 g, 88%) in analogy to the procedure for the preparation of (6S,7S)-7-(4,4-dimethyl-2-oxo-1-(2-propyl)-1,2,3,4-tetrahydroquinolin-6-yl)-6,7-methano-3-methyl-octa-2E, 4E-dienoic acid (Compound 1).

$^1$H-NMR (300 MHz, CDCl$_3$):d 1.11 (t, J=4.8 Hz,1H), 1.19–1.30(m,1H), 1.22(s, 3H),1.28(s, 3H), 1.40(s, 3H), 1.52 (s, 9H), 1.59–1.75(m, 3H), 2.00(s, 3H), 3.65–3.79(m, 2H), 5.30(dd, J=10.3, 15.4 Hz, 1H), 5.65(s, 1H), 6.23(d, J=15.5 Hz, 1H), 7.03(d, J=8.6 Hz, 1H), 7.12(s, 1H), 7.58(d, J=8.4 Hz, 1H).

7-Bromo-4,4-dimethyl-1-trifluoroacetyl-1,2,3,4-tetrahydroquinoline

Compound 29

A stirred, cooled (ice-bath) solution of 7-bromo-4,4-dimethyl-1,2,3,4-tetrahydroquinoline 28 (1.45 g, 6.06 mmol) in 20 mL of anhydrous dichloromethane was treated sequentially with 4-dimethylaminopyridine (1.6 g, 12.9 mmol) and trifluoroacetic anhydride (1.5 mL, 10.32 mmol. After 5 minutes, the reaction mixture was diluted with dichloromethane (30 mL) and washed with water (30 mL). The organic phase was dried over anhydrous sodium sulfate and the solvent evaporated in vacuo to give a residue, which on flash column chromatography over silica gel using 3% ethyl acetate in hexane as the eluent afforded the title compound (2.0 g, quantitative yield) as a white solid.

$^1$H-NMR (300 MHz, CDCl$_3$):d 1.32(s, 6H), 1.89(t, J=5.9 Hz, 2H), 3.84(t, J=5.6 Hz, 2H), 7.25(d, J=8.4 Hz, 1H), 7.26(s, 1H), 7.35(dd, J=8.4, 2.1 Hz, 1H).

4,4-Dimethyl-1,2,3,4-tetrahydroquinoline-7-boronic acid

Compound 30

7-bromo-4,4-dimethyl-1-trifluroacetyl-1,2,3,4-tetrahydroquinoline (Compound 29 2.0 g, 5.9 mmol) was converted into the title compound (0.6 g, 50%) in analogy to the procedure for the preparation of 4,4-dimethyl-2-oxo-1-(2-propyl)-1,2,3,4-tetrahydroquinoline-6-boronic acid (Compound 7). The product was used in the next step without any purification.

4,4-Dimethyl-7-(3-hydroxy-1-methyl-prop-1(Z)-enyl)-1,2,3,4-tetrahydroquinoline

Compound 31

4,4-Dimethyl-1,2,3,4-tetrahydroquinoline-7-boronic acid (Compound 30 0.6 g, 2.99 mmol) was converted into the title compound (0.46 g, 66%) in analogy to the procedure for the preparation of 4,4-dimethyl-6-(3-hydroxy- 1-methyl-prop-1(Z)-enyl)-2-oxo-1-(2-propyl)-1,2,3,4-tetrahydroquinoline (Compound 9).
$^1$H-NMR (300 MHz, CDCl$_3$):d 1.30(s, 6H), 1.74(t, J=5.9 Hz, 2H), 2.03(d, J=1.1 Hz, 3H), 3.30(t, J=5.8 Hz, 2H), 4.09(d, J=7.1 Hz, 2H), 5.65(dt, 1.2, 7.1 Hz, 1H), 6.29(d, J=1.7 Hz, 1H), 6.46(dd, J=7.8, 2.1 Hz, 1H), 7.13(d, J=7.8 Hz, 1H).

1-Acetyl-4,4-dimethyl-7-(3-hydroxy-1-methyl-prop-1(Z)-enyl)-1,2,3,4-tetrahydroquinoline

Compound 32

A stirred, cooled(ice bath) solution of 4,4-dimethyl-7-(3-hydroxy-1-methyl-prop-1(Z)-enyl)-1,2,3,4-tetrahydroquinoline (Compound 31 0.46 g, 2 mmol) in 10 mL of anhydrous dichloromethane was treated sequentially with triethylamine (1.8 mL, 12 mmol) and acetyl chloride (0.43 mL, 6 mmol) under argon. The reaction mixture was allowed to warm to room temperature and stirred for 2 hours. Then it was diluted with dichloromethane (15 mL) and washed with water (25 mL) and aqueous, dilute hydrochloric acid (25 mL). The organic phase was dried over anhydrous sodium sulfate and the solvent evaporated in vacuo to give a residue which was dissolved in 15 mL of 1:1 methanol:tetrahydrofuran and treated with a solution of lithium hydroxide (0.31 g, 7.4 mmol) in water (1.8 mL). The resulting clear, yellow solution was stirred at room temperature for 2 hours. The volatiles were removed by distillation in vacuo and the residue was diluted with water (25 mL) and extracted with ether (2×30 mL). The combined organic extract was dried over anhydrous sodium sulfate and the solvent evaporated in vacuo to give a residue which on flash column chromatography on silica gel (230–400 mesh) using 50% ethyl acetate in hexane as the eluent afforded 0.42 g (77%) of the title -compound as a viscous oil.
$^1$H-NMR (300 MHz, CDCl$_3$):d 1.30(s, 6H), 1.58(s, 1H), 1.80(t, J=6.3 Hz, 2H), 2.08(d, J=1.1 Hz, 3H), 2.26(s, 3H), 3.83(t, J=6.0 Hz, 2H), 4.09(d, J=7.0 Hz, 2H), 5.74(dt, 1.5, 7.2 Hz, 1H), 6.98(dd, J=8.0,1.7 Hz, 1H), 7.26(s, 1H) 7.29(d, J=8.0 Hz, 1H).

1-Acetyl-4,4-dimethyl-7-[(1S,2S)-3-hydroxy-1,2-methano-1-methyl-propyl]-1,2,3,4-tetrahydroquinoline

Compound 33

1-Acetyl-4,4-dimethyl-7-(3-hydroxy-1-methyl-prop-1 (Z)-enyl)-1,2,3,4-tetrahydroquinoline (Compound 32 0.42 g, 1.53 mmol) was converted into the title compound (0.39 g, 90%) as a pale yellow, viscous oil in analogy to the procedure for the preparation of 4,4-dimethyl-6-[(1S,2S)-3-hydroxy-1,2-methano-1-methyl-propyl]-2-oxo-1-(2-propyl)-1,2,3,4-tetrahydroquinoline (Compound 11).
$^1$H-NMR (300 MHz, CDCl$_3$):d 0.71–0.74(m, 2H), 1.19–1.31(m, 7H), 1.33(s, 3H), 1.74(t, J=6.2 Hz, 2H), 2.21 (s, 3H), 2.90–3.25(br m, 1H), 3.25–3.50(br m, 1H), 3.65–3.84(m, 2H), 7.04(d, J=7.4 Hz, 1H)), 7.2(d, J=8.0 Hz, 1H).

(1S)-Camphanate ester of 1-Acetyl-4,4-dimethyl-7-[(1S,2S)-3-hydroxy-1,2-methano-1-methyl-propyl]-1,2,3,4-tetrahydroquinoline

Compound 34

1-Acetyl-4,4-dimethyl-7-[(1S,2S)-3-hydroxy-1,2-methano-1-methyl-propyl]-1,2,3,4-tetrahydroquinoline (Compound 33 0.39 g, 1.38 mmol) was converted to its (1S)-camphanate ester (Compound 34 0.40 g, 62% after HPLC) in analogy to the procedure for the preparation of (1S)-camphanate ester of 4,4dimethyl-6-[(1S,2S)-3-hydroxy-1,2-methano-1-methyl-propyl]-2-oxo-1-(2-propyl)-1,2,3,4-tetrahydroquinoline (Compound 12). The product was purified on a preparative normal phase HPLC column using 50% ethyl acetate in hexane as the mobile phase.
$^1$H-NMR (300 MHz, CDCl$_3$): d 0.81–0.91(m, 2H), 0.91(s, 3H), 0.99(s, 3H), 1.07(s, 3H), 1.21–1.26(m, 1H), 1.22(s, 3H), 1.24(s, 3H), 1.35(s, 3H), 1.65-1.75(m, 1H), 1.72(t, J=6.5 Hz, 2H), 1.83–2.02(m, 2H), 2.20(s, 3H), 2.28–2.38(m, 1H), 3.63–3.91(m, 4H), 7.05(dd, J=1.6, 8.1 Hz, 1H), 7.20(d, J=8.1 Hz, 1H).

1-Acetyl-4,4-dimethyl-7-[(1S,2S)-3-hydroxy-1,2-methano-1-methyl-propyl]-1,2,3,4-tetrahydroquinoline

Compound 33

(1S)-Camphanate ester of 1-acetyl-4,4-dimethyl-7-[(1S, 2S)-3-hydroxy-1,2-methano-1-methyl-propyl]-1,2,3,4-tetrahydroquinoline (Compound 34 0.4 g, 0.85 mmol) was hydrolyzed to the title compound (0.22 g, 90%) in analogy to the procedure for the preparation of 4,4-dimethyl-6-[(1S, 2S)-3-hydroxy-1,2-methano-1-methyl-propyl]-2-oxo-1-(2-propyl)-1,2,3,4-tetrahydroquinoline (Compound 13).
$^1$H-NMR (300 MHz, CDCl$_3$): d 0.71–0.74(m, 2H), 1.19–1.31(m, 7H), 1.33(s, 3H), 1.74(t, J=6.2 Hz, 2H), 2.21 (s, 3H), 2.90–3.25(br m, 1H), 3.25–3.50(br m, 1H), 3.65–3.84(m, 2H), 7.04(d, J=7.4Hz, 1H)), 7.2(d, J=8.0 Hz, 1H).

1-Acetyl-4,4-dimethyl-7-[(1S,2S)-1,2-methano-1-methyl-3-oxo-propyl]-1,2,3,4-tetrahydroquinoline

Compound 35

1-Acetyl-4,4-dimethyl-7-[(1S,2S)-3-hydroxy-1,2-methano-1-methyl-propyl]-1,2,3,4-tetrahydroquinoline (Compound 33 0.13 g, 0.45 mmol) was oxidized to give the title compound (0.11 g, 84%) in analogy to the procedure for the preparation of 4,4-dimethyl-6-[(1S,2S)-3-oxo-1,2-methano-1-methyl-propyl]-2-oxo-1-(2-propyl)-1,2,3,4-tetrahydroquinoline (Compound 14).
$^1$H-NMR (300 MHz, CDCl$_3$):d 1.21(s, 6H), 1.35–1.41(m, 1H), 1.41(s, 3H), 1.70(t, J=6.2 Hz, 2H), 1.82(t, J=5.0 Hz, 1H), 1.89–1.97(m, 1H), 2.16(s, 3H), 3.71–3.78(m, 2H), 7.04(d, J=8.2 Hz, 1H), 7.20(d, J=7.8 Hz, 1H), 8.46(d, J=6.7 Hz, 1H).

(6S,7S)-7-(1-Acetyl-4,4-dimethyl-1,2,3,4-tetrahydroquinolin-7yl)-6,7-methano-3-methyl-octa-2E,4E-dienoic acid ethyl ester Compound 36

1-(Acetyl)-4,4-dimethyl-7-[(1S,2S)-1,2-methano-1-methyl-3-oxo-propyl]-1,2,3,4-tetrahydroquinoline (Compound 35 0.11 g, 0.38 mmol) was converted into the title compound (0.13 g, 85%) in analogy to the procedure for the preparation of (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid ethyl ester (Compound 15). (The 3E isomer was formed to an extent of ~4%.)
$^1$H-NMR (300 MHz, CDCl$_3$): d 1.14–1.24(m, 2H), 1.27(t, J=7.3 Hz, 3H), 1.27(s, 6H), 1.41(s, 3H), 1.76(m, 3H), 1.96(s, 3H), 2.17(s, 3H), 3.71–3.76(m, 1H), 3.78–3.90(m, 1H), 4.13(q, J=7.1 Hz), 5.17(dd, J=9.9, 15.6 Hz, 1H), 5.62(s, 1H), 6.18(d, J=15.5 Hz, 1H), 7.03(d, J=8.1 Hz, 1H), 7.24(d, J=8.0 Hz, 1H).

(6S,7S)-1-Acetyl-4,4-dimethyl-1,2,3,4-tetrahydroquinolin-7-yl)-6.7-methano-3-methyl-octa-2E,4E-dienoic acid Compound 26

(6S,7S)-7-(1-Acetyl-4,4-dimethyl-1,2,3,4-tetrahydroquinolin-6-yl)-6,7-methano-3-methyl-octa-2E,4E-dienoic acid ethyl ester (Compound 36 0.1 g, 0.25 mmol) was hydrolyzed to give the title compound (0.55 g, 59% after HPLC) in analogy to the procedure for the preparation of (6S,7S)-7-(4,4-dimethyl-2-oxo-1-(2-propyl)-1,2,3,4-tetrahydroquiolin-6-yl)-6,7-methano-3-methyl-octa-2E,4E-dienoic acid (Compound 1). The product was purified by preparative reverse phase HPLC using 12% water in acetonitrile as the mobile phase.
$^1$H-NMR (300 MHz, CDCl$_3$): d 1.13–1.25(m, 2h), 1.25(s, 3H), 1.27(s, 3H), 1.40(s, 3H), 1.75(t, J=6.2 Hz, 2H), 1.71–1.79(m, 1H), 1.94(s, 3H), 2.16(s, 3H), 3.67–3.76(m, 1H), 3.80–3.95(m, 1H), 5.19(dd, J=9.9, 15.4 Hz, 1H), 5.63 (s, 1H), 6.19(d, J=15.5 Hz, 1H), 7.03(d, J=7.8 Hz, 1H), 7.23(d, J=8.0 Hz, 1H).

1-Acetyl-4,4-dimethyl-6-[(1S,2D)-3-hydroxy-1,2-methano-1-methyl-propyl]-1,2,3,4-tetrahydro-quinoline Compound 37

A stirred, cooled (ice bath) solution of the (1S)-camphanate ester of 1-(tert-butyloxycarbonyl)-4,4-dimethyl-6-[(1S,2S)-3-hydroxy-1,2-methano-1-methyl-propyl]-1,2,3,4-tetrahydro-quinoline (Compound 23 0.11 g, 0.21 mmol) in 4 mL of anhydrous dichloromethane was treated with 1 mL of trifluoroacetic acid and stirred at 0° C. for 15 minutes and at room temperature for 0.5 hours. The reaction mixture was diluted with 20 mL of dichloromethane and neutralized with saturated, aqueous sodium bicarbonate solution. The organic phase was dried over anhydrous sodium sulfate and the solvents were evaporated in vacuo to afford 0.1 g of a yellow oil. The oil was dissolved in 3 mL of anhydrous dichloromethane, cooled in an ice bath and treated sequentially with 4-dimethylaminopyridine (0.122 g, 1 mmol) and acetyl chloride (0.05 mL, 0.5 mmol). The reaction mixture was allowed to warm to room temperature and stirred for 1 hour at the end of which dichloromethane was added (20 mL) and the organic phase was washed with water (20 mL). The organic phase was dried over anhydrous sodium sulfate and the solvents were evaporated under reduced pressure to afford 0.1 g of a solid that was again dissolved in 3 mL of 1:1 methanol:tetrahydrofuran and treated with 1 mL of 1M sodium hydroxide solution. After stirring at room temperature for 1.5 hours, the reaction mixture was concentrated under reduced pressure. The residue was diluted with water (20 mL) and extracted with diethylether (2×20 mL). The combined organic extract was dried over anhydrous sodium sulfate and the solvent was evaporated i vacuo to give a yellow oil which was subjected to flash column chromatography on silica gel (230–400 mesh) using 50% ethyl acetate in hexane as the eluent to afford the title compound (0.045 g, 72%) as a pale yellow oil..
$^1$H-NMR (300 MHz, CDCl$_3$):d 0.81–0.87(m, 2H), 1.26–132 (m, 1H), 1.29(s, 6H), 1.39(s, 3H), 1.77(t, J=6.5 Hz, 2H), 2.23(s, 3H), 3.24(d, J=7.1 Hz, 2H), 3.80(t, J=6.2 Hz, 2H), 7.13(dd, J=2.0, 8.2 Hz, 1H), 7.28(d, J=2.2 Hz, 1H).

1-Acetyl-4,4-dimethyl-6-[(1S,2S)-1.2-methano-1-methyl-3-oxo-propyl]-1,2,3,4-tetrahydro-quinoline Compound 38

1-Acetyl-4,4-dimethyl-6-[(1S,2S)-3-hydroxy-1,2-methano-1-methyl-propyl]-1,2,3,4-tetrahydro-quinoline (Compound 37 0.045 g, 0.15 mmol) was oxidized to provide the title compound (0.04, 89%) in analogy to the procedure for the preparation of 4,4-dimethyl-6-[(1S,2S)-3-oxo-1,2-methano-1-methyl-propyl]-2-oxo-1-(2-propyl)-1,2,3,4-tetrahydroquinoline (Compound 14).
$^1$H-NMR (300 MHz, CDCl$_3$): d 1,25(s, 3H), 1.27(s, 3H), 13.9–1.45(m, 1H), 1.45(s, 3H), 1.75(t, J=6.5 Hz, 2H), 1.86(t, J=4.9 Hz, 1H), 1.92–1.98(m, 1H), 2.21(s, 3H), 3.76 (unresolved t, 2H), 7.12(d, J=8.0 Hz, 1H), 7.25(d, J=3.0 Hz, 1H), 8.44(d, J=7.01 Hz, 1H).

(6S,7S)-7-(1-Acetyl-4,4-dimethyl-1,2,3,4-tetrahydro-quinolin-6-yl)-6,7-methano-3-methyl-octa-2E,4E-dienoic acid ethyl ester Compound 43

1-Acetyl-4,4-dimethyl-6-[(1S,2S)-1,2-methano-1-methyl-3-oxo-propyl]-1,2,3,4-tetrahydro-quinoline (Compound 38 0.04 g, 0.14 mmol) was converted into the title compound (0.033 g, 59% after preparative reverse phase HPLC using 12% water in acetonitrile as the mobile phase) in analogy to the procedure for the preparation of (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid ethyl ester (Compound 15). The 3E isomer was formed to an extent of ~4%.
$^1$H-NMR (300 MHz, CDCl$_3$):d 1.15(t, J=4.9 Hz, 1H), 1.19–1.27(m, 4H), 1.22(s, 3H), 1.26(s, 3H), 1.41(s, 3H), 1.69–1.81(m, 3H), 1.97(s, 3H), 2.21(s, 3H), 3.69–3.91(m, 2H), 4.12(q, J=7.1 Hz), 5.18(dd, J=9.9, 15.4 Hz, 1H), 5.62(s, 1H), 6.18(d, J=15.5 Hz, 1H), 7.06(d, J=7.8 Hz, 1H), 7.24(s, 1H).

(6S,7S)-7-(1-(Acetyl)-4,4-dimethyl-1,2,3,4-tetrahydro-quinolin-6-yl)-6,7-methano-3-methyl-octa-2E,4E-dienoic acid Compound 40

(6S,7S)-7-(1-Acetyl-4,4-dimethyl-1,2,3,4-tetrahydro-quinolin-6-yl)-6,7-methano-3-methyl-octa-2E,4E-dienoic acid ethyl ester (Compound 0.033 g, 0.083 mmol) was hydrolyzed to provide the title compound (0.022g, 72%) in analogy to the procedure for the preparation of (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid (Compound 1). The product was purified by flash column chromatography on silica gel(230–400 mesh) using 60% ethyl acetate in hexane as the eluent.

$^1$H-NMR (300 MHz, CDCl$_3$):d 1.16(t, J=4.9 Hz, 1H), 1.20–1.31(m, 1H), 1.23(s, 3H), 1.286(s, 3H), 1.43(s, 3H), 1.69–1.81(m, 3H), 1.98(s, 3H), 2.231(s, 3H), 3.70–3.91(m, 2H), 5.24(dd, J=9.9, 15.4 Hz, 1H), 5.66(s, 1H), 6.22(d, J=16.5 Hz, 1H), 7.07(d, J=8.0 Hz, 1H), 7.17(s, 1H).

What is claimed is:

1. A compound of Formula 1

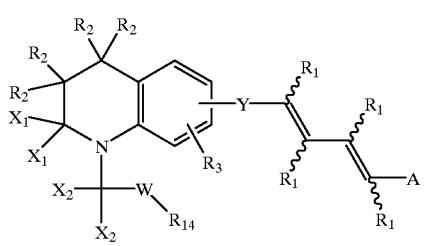

Formula 1 where Y is a bivalent radical having Formula 3

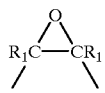

Formula 3 the two $X_1$ groups jointly represent an oxo (=O) or thione (=S) function, or $X_1$ is independently selected from H or alkyl of 1 to 6 carbons;

the two $X_2$ groups jointly represent an oxo (=O) or a thione (=S) function, or $X_2$ is independently selected from H or alkyl of 1 to 6 carbons, with the proviso that one of the joint $X_1$ grouping or of the joint $X_2$ grouping represents an oxo (=O) or a thione (=S) function;

W is O, C(R$_1$)$_2$, or W does not exist;

$R_1$ is independently H, lower alkyl of 1 to 6 carbons, or lower fluoroalkyl of 1 to 6 carbons;

$R_2$ is independently H, lower alkyl of 1 to 6 carbons, or lower fluoroalkyl of 1 to 6 carbons;

$R_3$ is hydrogen, lower alkyl of I to 6 carbons, OR$_1$, fluoro substituted lower alkyl of 1 to 6 carbons or halogen, NO$_2$, NH$_2$, NHCO(C$_1$–C$_6$ alkyl, or NHCO(C$_1$–C$_6$) alkenyl;

A is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CH(OR$_{13}$O), —COR$_7$, CR$_7$(OR$_{12}$)$_2$, CR$_7$(OR$_{13}$O), or Si(C$_{1-6}$alkyl)$_3$, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl, hydroxyphenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, and $R_{14}$ is H, alkyl of 1 to 10 carbons, fluoro-substituted alkyl of 1 to 10 carbons, alkenyl of 2 to 10 carbons and having 1 to 3 double bonds.

2. A compound in accordance with claim 1 where the two $X_1$ groups jointly represent an oxo (=O) or thione (=S) function.

3. A compound in accordance with claim 1 where the two $X_2$ groups jointly represent an oxo (=O) or a thione (=S) function.

4. A compound of the formula

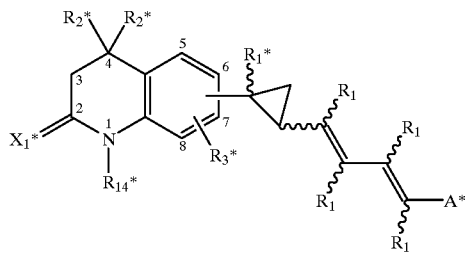

wherein $R_1$ is independently H, lower alkyl of 1 to 6 carbons, or lower fluoroalkyl of 1 to 6 carbons;

$R_1^*$ is hydrogen or $C_{1-6}$-alkyl;

$R_2^*$ is independently H, lower alkyl of 1 to 6 carbons, or lower fluoroalkyl of 1 to 6 carbons;

$R_3^*$ is hydrogen, lower alkyl of 1 to 6 carbons, fluoro substituted lower alkyl of 1 to 6 carbons or halogen;

$X_1^*$ is an oxo (=O) or a thione (=S) group;

A* is hydrogen, COOH or a pharmaceutically acceptable salt thereof, COOR$_8$, CONR$_9$R$_{10}$, where R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl, hydroxyphenyl or lower alkylphenyl, and the cyclopropyl group is attached to the 6 or 7 position of the tetrahydroquinoline moiety, and $R_{14}^*$ is alkyl of 1 to 10 carbons or fluoro-substituted alkyl of 1 to 10 carbons.

5. A compound in accordance with claim 4 where $R_2^*$ is CH$_3$.

6. A compound in accordance with claim 5 where $R_1$ is H or CH$_3$.

7. A compound in accordance with claim 6 where $R_3^*$ is H.

8. A compound in accordance with claim 7 where $R_{14}^*$ is lower alkyl of 1 to 6 carbons.

9. A compound in accordance with claim 8 where the cyclopropyl group is attached to the 6 position of the tetrahydroquinoline moiety.

10. A compound in accordance with claim 9 where the configuration about the cyclopropyl ring is cis, and the configurations about the double bonds are trans.

11. A compound in accordance with claim 10 where A* is COOH or a pharmaceutically acceptable salt thereof, or COOR$_8$.

12. A compound in accordance with claim 11 where $R_{14}^*$ is iso-propyl.

13. A compound in accordance with claim 12 where $R_1^*$ is methyl.

14. A compound in accordance with claim 4, selected from the group consisting of:

(6S,7S)-7-(4,4-dimethyl-2-oxo-1-(2-propyl)-1,2,3,4-tetrahydroquinolin-6-yl)-6,7-methano-3-methyl-octa-2E,4E-dienoic acid, (6S,7S)-7-(4,4-dimethyl-2-oxo-1-(2-propyl)-1,2,3,4-tetrahydroquinolin-6-yl)-6,7-methano-3-methyl-octa-2E,4E-dienoic acid ethyl ester, (6S,7S)-7-(4,4-dimethyl-1-(2-propyl)-2-thioxo-1,2,3,4-tetrahydroquinolin-6-yl)-6,7-methano-3-methyl-octa-2E,4E-dienoic acid ethyl ester, and (6S,7S)-7-(4,4-dimethyl-1-(2-propyl)-2-thioxo-1,2,3,4-tetrahydroquinolin-6-yl)-6,7-methano-3-methyl-octa-2E,4E-dienoic acid.

15. A compound of the formula

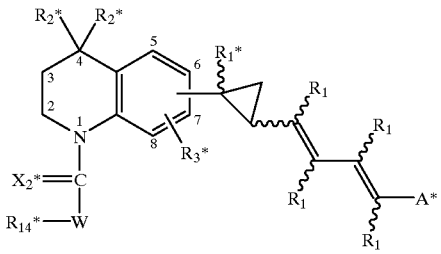

wherein $R_1$ is independently H, lower alkyl of 1 to 6 carbons, or lower fluoroalkyl of 1 to 6 carbons;

$R_1^*$ is hydrogen or $C_{1-6}$-alkyl;

$R_2^*$ is independently H, lower alkyl of 1 to 6 carbons, or lower fluoroalkyl of 1 to 6 carbons;

$R_3^*$ is hydrogen, lower alkyl of 1 to 6 carbons, fluoro substituted lower alkyl of 1 to 6 carbons or halogen;

$X_2^*$ is an oxo (=O) or a thione (=S) group;

A* is hydrogen, COOH or a pharmaceutically acceptable salt thereof, $COOR_8$, $CONR_9R_{10}$, where $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, and the cyclopropyl group is attached to the 6 or 7 position of the tetrahydroquinoline moiety, W* O, CH or $CH_2$, with the proviso that when W* is CH then there are two $R_{14}^*$ groups attached to it, and $R_{14}^*$ is H, alkyl of 1 to 10 carbons or fluoro-substituted alkyl of 1 to 10 carbons.

16. A compound in accordance with claim 15 where $R_2^*$ is $CH_3$.

17. A compound in accordance with claim 16 where $R_1$ is H or $CH_3$.

18. A compound in accordance with claim 17 where $R_3^*$ is H.

19. A compound in accordance with claim 18 where $R_{14}^*$ is lower alkyl of 1 to 6 carbons.

20. A compound in accordance with claim 19 where the configuration about the cyclopropyl ring is cis, and the configurations about the double bonds are trans.

21. A compound in accordance with claim 20 where A* is COOH or a pharmaceutically acceptable salt thereof, or $COOR_8$.

22. A compound in accordance with claim 21 where $R_{14}^*$ is methyl or tertiary-butyl.

23. A compound in accordance with claim 22 where $R_1^*$ is methyl.

24. A compound in accordance with claim 15, selected from the group consisting of:

(6S,7S)-7-(1-(tert-butyloxycarbonyl)-4,4-dimethyl-1,2,3,4-tetrahydroquinolin-6-yl)-6,7-methano-3-methyl-octa-2E,4E-dienoic acid, (6S,7S)-7-(1-(tert-butyloxycarbonyl)-4,4-dimethyl-1,2,3,4-tetrahydroquinolin-6-yl)-6,7-methano-3-methyl-octa-2E,4E-dienoic acid ethyl ester, (6S,7S)-7-(1-(Acetyl)-4,4-dimethyl-1,2,3,4-tetrahydroquinolin-6-yl)-6,7-methano-3-methyl-octa-2E,4E-dienoic acid, (6S,7S)-7-(1-Acetyl-4,4-dimethyl-1,2,3,4-tetrahydroquinolin-6-yl)-6,7-methano-3-methyl-octa-2E,4E-dienoic acid ethyl ester, (6S,7S)-1-Acetyl-4,4-dimethyl-1,2,3,4-tetrahydroquinolin-7-yl)-6,7-methano-3-methyl-octa-2E,4E-dienoic acid, and (6S,7S)-7-(1-Acetyl-4,4-dimethyl-1,2,3,4-tetrahydroquinolin-7-yl)-6,7-methano-3-methyl-octa-2E,4E-dienoic acid ethyl ester.

* * * * *

UNITED STATES PATENT AND TRADEMARK OFFICE
CERTIFICATE OF CORRECTION

PATENT NO.   : 6,048,873
DATED        : April 11, 2000
INVENTOR(S)  : Vasudevan et al.

It is certified that error appears in the above-identified patent and that said Letters Patent is hereby corrected as shown below:

Title Page,
Line 1, "TETRAHDROQUINOLIN" should be -- TETRAHYDROQUINOLIN --.
Line 2, "TETRAHDROQUINILIN" should be -- TETRAHYDROQUINILIN --.

Column 1,
Line 1, "TETRAHDROQUINOLIN" should be -- TETRAHYDROQUINOLIN --.
Line 2, "TETRAHDROQUINILIN" should be -- TETRAHYDROQUINILIN --.

Column 2,
Line 20, after "in", delete "is".

Column 4,
Line 3, "cycloayl" should be -- cycloalkyl --.

Column 5,
Line 3, after "carbons", delete ",".
Line 7, "$CH_2OR,_{11}$" should be -- $CH_2OR_{11}$ --.
Line 24, "$C_1$-$C_{10}$-alkylphenyl" should be -- $c_1$-$c_{10}$-alkylphenyl --.

Column 9,
Line 35, TABLE 2, Compound 17,
">30,000   10,000   12,000" should be
-- 12,000   >30,000   10,000 --.

Column 16,
Line 31, "R," should be -- $R_2$ --.

Column 23,
Line 63, "4,4dialkyl" should be -- 4,4-dialkyl --.

Column 34,
Line 13, "2,2 Hz" should be -- 2.2 Hz --.
Line 36, "1I" should be -- 1H --.

UNITED STATES PATENT AND TRADEMARK OFFICE
CERTIFICATE OF CORRECTION

PATENT NO. : 6,048,873
DATED : April 11, 2000
INVENTOR(S) : Vasudevan et al.

It is certified that error appears in the above-identified patent and that said Letters Patent is hereby corrected as shown below:

Column 35,
Line 13, "-25+C." should be -- -25°C --.
Line 31, after "propyl", insert -- ) --.
Line 65, after "tetrahydroquinoline", insert -- ( --.

Column 38,
Line 8, "J24.7 Hz" should be -- 00J=24.7 Hz --.
Line 9, "J9.9" should be -- J=9.9 --.
Line 9, delete "1s".
Line 9,"J15.5 Hz" should be -- J15.5 Hz --.
Line 12, "butyloxycarbonal" should be -- butyloxy-carbonyl --.

Column 39,
Line 43, after "4,4", insert -- - --.

Column 43,
Line 2, "7yl" should be -- 7-yl --.

Column 44,
Line 10, after "evaporated", "i" should be -- in --.
Line 15, "132" should be -- 1.32 --.

Column 45,
Line 30, the structure of Formula 3 should be
--                           --

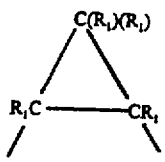

Line 49, "I" should be -- 1 --.

UNITED STATES PATENT AND TRADEMARK OFFICE
CERTIFICATE OF CORRECTION

PATENT NO.   : 6,048,873
DATED        : April 11, 2000
INVENTOR(S)  : Vasudevan et al.

It is certified that error appears in the above-identified patent and that said Letters Patent is hereby corrected as shown below:

Column 5,
Line 44, after "bond", delete the second occurrence of ".".

Column 7,
Line 9, "co-tranfection" should be -- co-transfection --.
Line 66, "ug/well" should be -- µg/well --.

Column 8,
Line 1, "ug/well" should be -- µg/well --.
Line 2, "ug/well" should be -- µg/well --.
Line 19, "ug/well" should be -- µg/well --.

Column 21,
Line 23, after "CDCl$_3$):", "d" should be -- 8 --.
Line 66, delete the second occurrence of "is".

Column 33,
Line 37, after "CDCl$_3$):", "d" should be -- 8 --.
Line 57, after "CDCl$_3$):", "d" should be -- 8 --.

Column 34,
Line 11, after "CDCl$_3$):", "d" should be -- 8 --.
Line 34, after "CDCOCD$_3$):", "d" should be -- 8 --.
Line 57, after "CDCl$_3$):", "d" should be -- 8 --.

Column 35,
Line 23, after "CDCl$_3$):", "d" should be -- 8 --.
Line 50, after "CDCl$_3$):", "d" should be -- 8 --.

Column 36,
Line 9, after "CDCl$_3$):", "d" should be -- 8 --.
Line 32, after "CDCl$_3$):", "d" should be -- 8 --.
Line 64, after "CDCl$_3$):", "d" should be -- 8 --.

UNITED STATES PATENT AND TRADEMARK OFFICE
CERTIFICATE OF CORRECTION

PATENT NO. : 6,048,873
DATED : April 11, 2000
INVENTOR(S) : Vasudevan et al.

It is certified that error appears in the above-identified patent and that said Letters Patent is hereby corrected as shown below:

Column 37,
Line 26, after "CDCl$_3$):", "d" should be -- 8 --.
Line 27, after "1.23 (s, 3H", insert -- ) --.
Line 51, after "CDCl$_3$):", "d" should be -- 8 --.
Line 52, after "J=7.1 Hz, 3H", insert -- ) --.

Column 38,
Line 6, after "CDCl$_3$):", "d" should be -- 8 --.
Line 29, after "CDCl$_3$):", "d" should be -- 8 --.
Line 56, after "CDCl$_3$):", "d" should be -- 8 --.

Column 39,
Line 7, after "CDCl$_3$):", "d" should be -- 8 --.
Line 28, after "CDCl$_3$):", "d" should be -- 8 --.
Line 50, after "CDCl$_3$):", "d" should be -- 8 --.

Column 40,
Line 1, after "CDCl$_3$):", "d" should be -- 8 --.
Line 22, after "CDCl$_3$):", "d" should be -- 8 --.
Line 42, after "CDCl$_3$):", "d" should be -- 8 --.
Line 65, after "CDCl$_3$):", "d" should be -- 8 --.

Column 41,
Line 5, "trifluroacetyl" should be -- trifluoroacetyl --.
Line 55, after "CDCl$_3$):", "d" should be -- 8 --.

Column 42,
Line 6, after "CDCl$_3$):", "d" should be -- 8 --.
Line 28, after "CDCl$_3$):", "d" should be -- 8 --.
Line 46, after "CDCl$_3$):", "d" should be -- 8 --.
Line 63, after "CDCl$_3$):", "d" should be -- 8 --.

UNITED STATES PATENT AND TRADEMARK OFFICE
CERTIFICATE OF CORRECTION

PATENT NO. : 6,048,873
DATED : April 11, 2000
INVENTOR(S) : Vasudevan et al.

Page 5 of 5

It is certified that error appears in the above-identified patent and that said Letters Patent is hereby corrected as shown below:

Column 43,
Line 14, after "CDCl$_3$):", "d" should be -- 8 --.
Line 37, after "CDCl$_3$):", "d" should be -- 8 --; "2h" should be -- 2H --.

Column 44,
Line 14, delete the second occurrence of ".".
Line 15, after "CDCl$_3$):", "d" should be -- 8 --.
Line 31, after "CDCl$_3$):", "d" should be -- 8 --.
Line 53, after "CDCl$_3$):", "d" should be -- 8 --.

Column 45,
Line 8, after "CDCl$_3$):", "d" should be -- 8 --.

Signed and Sealed this

Twenty-seventh Day of November, 2001

*Attest:*

*Attesting Officer*

NICHOLAS P. GODICI
*Acting Director of the United States Patent and Trademark Office*